(12) United States Patent
Laghi

(10) Patent No.: US 11,389,326 B2
(45) Date of Patent: Jul. 19, 2022

(54) PHASE CHANGE MATERIAL FOR THERMAL THERAPY AND DELIVERY OF ACTIVE INGREDIENTS

(71) Applicant: Alps South, LLC, St. Petersburg, FL (US)

(72) Inventor: Aldo Laghi, Clearwater, FL (US)

( * ) Notice: Subject to any disclaimer, the term of this patent is extended or adjusted under 35 U.S.C. 154(b) by 706 days.

(21) Appl. No.: 15/656,564

(22) Filed: Jul. 21, 2017

(65) Prior Publication Data
US 2018/0021169 A1    Jan. 25, 2018

Related U.S. Application Data

(63) Continuation-in-part of application No. 14/602,893, filed on Jan. 22, 2015, now abandoned.
(Continued)

(51) Int. Cl.
*A61F 7/02* (2006.01)
*A61F 7/00* (2006.01)
(Continued)

(52) U.S. Cl.
CPC .............. *A61F 7/02* (2013.01); *A61F 7/00* (2013.01); *A61F 13/00063* (2013.01);
(Continued)

(58) Field of Classification Search
CPC . C08L 9/06; A61M 35/10; A61M 2037/0007; A61M 2205/0216;
(Continued)

(56) References Cited

U.S. PATENT DOCUMENTS

| | | | |
|---|---|---|---|
| 5,006,342 A | | 4/1991 | Cleary et al. |
| 5,452,712 A | * | 9/1995 | Richardson ............ A62B 17/04 |
| | | | 128/201.22 |

(Continued)

OTHER PUBLICATIONS

Araki, Takeo; Shibayama, Mitsuhiro; Tran-Cong, Qui. Structure and Properties of Multiphase Polymeric Materials. Kyoto, Japan. Mercel Dekker, Inc. 1998 (Year: 1998).*
(Continued)

*Primary Examiner* — Ophelia A Hawthorne
(74) *Attorney, Agent, or Firm* — GrayRobinson, P.A.

(57) ABSTRACT

A soft thermoformable elastomer with a phase change material exhibiting high latent heat of fusion. The compound provides elasticity, softness, formability, and heat over an extended duration and to facilitate prolonged skin contact at elevated temperatures. Used in combination with active ingredients the increased temperature and formability provides enhanced transdermal delivery through the skin. Thermoplastic elastomers may be manufactured by mixing together plasticizing oil, a triblock copolymer, a paraffinic substance and one or more additives, e.g., an antioxidant, an antimicrobial agent, and/or other additives to form a mixture which melted then cooled into the thermoplastic elastomer. During cooling, the thermoplastic elastomer may be molded or otherwise formed into any number of articles including, but not limited to, prosthetic liners, prosthetic sleeves, external breast prostheses, breast enhancement bladders, masks, wound dressing sheets, wound dressing pads, socks, gloves, malleolus pads, metatarsal pads, shoe insoles, urinary catheters, vascular catheters, and balloons for medical catheters both vascular as well as urinary. Active ingredients are preferably added to the cooling thermoplastic elastomer when the temperature is below 100° F. to prevent heat degradation and/or breakdown of vital proteins.

26 Claims, 32 Drawing Sheets

Related U.S. Application Data

(60) Provisional application No. 62/364,998, filed on Jul. 21, 2016.

(51) Int. Cl.
 *A61F 13/08* (2006.01)
 *A61F 13/00* (2006.01)
 *A61F 13/12* (2006.01)
 *A61M 35/00* (2006.01)
 *C08L 9/06* (2006.01)

(52) U.S. Cl.
 CPC .............. *A61F 13/08* (2013.01); *A61F 13/12* (2013.01); *A61M 35/10* (2019.05); *A61F 2007/001* (2013.01); *A61F 2007/0003* (2013.01); *A61F 2007/0004* (2013.01); *A61F 2007/0052* (2013.01); *A61F 2007/0228* (2013.01); *A61F 2007/0231* (2013.01); *A61F 2007/0244* (2013.01); *A61F 2007/0261* (2013.01); *A61F 2007/0292* (2013.01); *C08L 9/06* (2013.01)

(58) Field of Classification Search
 CPC .......... A61M 2205/05; A61M 2205/36; A61M 2205/362; A61M 2205/3633; A61F 2007/0002; A61F 2007/0003; A61F 2007/0209; A61F 2007/0214; A61F 2007/0219; A61F 2007/0225; A61F 2007/0231; A61F 2007/0244; A61F 2007/0249; A61F 2007/0261; A61F 2007/0292; A61F 7/02; A61F 13/00008; A61F 13/00017; A61F 13/00021; A61F 13/00029; A61F 7/00
 See application file for complete search history.

(56) References Cited

U.S. PATENT DOCUMENTS

| | | | |
|---|---|---|---|
| 5,565,132 A | 10/1996 | Salyer | |
| 6,019,101 A * | 2/2000 | Cotner | A61M 16/06 128/206.18 |
| 6,328,992 B1 | 12/2001 | Brooke et al. | |
| 7,709,570 B2 | 5/2010 | Laghi | |
| 9,050,348 B2 | 6/2015 | Kydonieus et al. | |
| 9,249,303 B2 | 2/2016 | Xu | |
| 2005/0187502 A1* | 8/2005 | Krempel | A61F 7/02 602/5 |
| 2009/0287280 A1 | 11/2009 | Wong | |
| 2012/0070543 A1 | 3/2012 | Mahlich | |
| 2012/0244312 A1* | 9/2012 | Pearce | D06N 7/0092 428/136 |
| 2014/0242127 A1 | 8/2014 | Yokozeki et al. | |
| 2014/0243471 A1* | 8/2014 | Xu | C08K 5/01 524/578 |
| 2016/0019764 A1 | 2/2016 | Chen | |
| 2016/0051402 A1 | 2/2016 | Laghi | |
| 2016/0051412 A1* | 2/2016 | Moreland | D04B 1/108 602/48 |

OTHER PUBLICATIONS

Vakhshouri, Amir Reza. Paraffin as Phase Change Material. IntechOpen. Published Dec. 15, 2019. Accessed Mar. 26, 2020. (Year: 2019).*
Araki, Takeo; Shibayama, Mitsuhiro; Tran-Cong, Qui. Structure and Properties of Multiphase Polymeric Materials. Kyoto, Japan. Mercel Dekker, Inc. 1998 (Year: 1998 (Year: 1998).*
Song, Chang W., https://www.ncbi.nlm.nih.gov/pubmed/2808037.

* cited by examiner

PRIOR ART

PRIOR ART

PRIOR ART

PRIOR ART

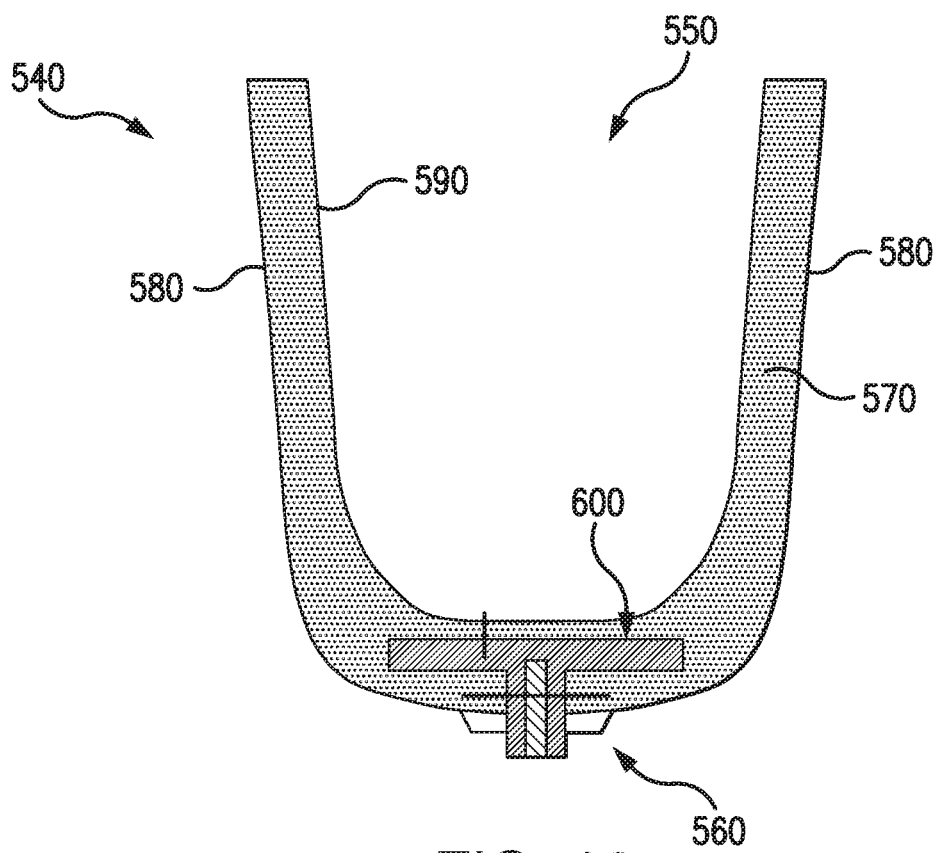
FIG. 13
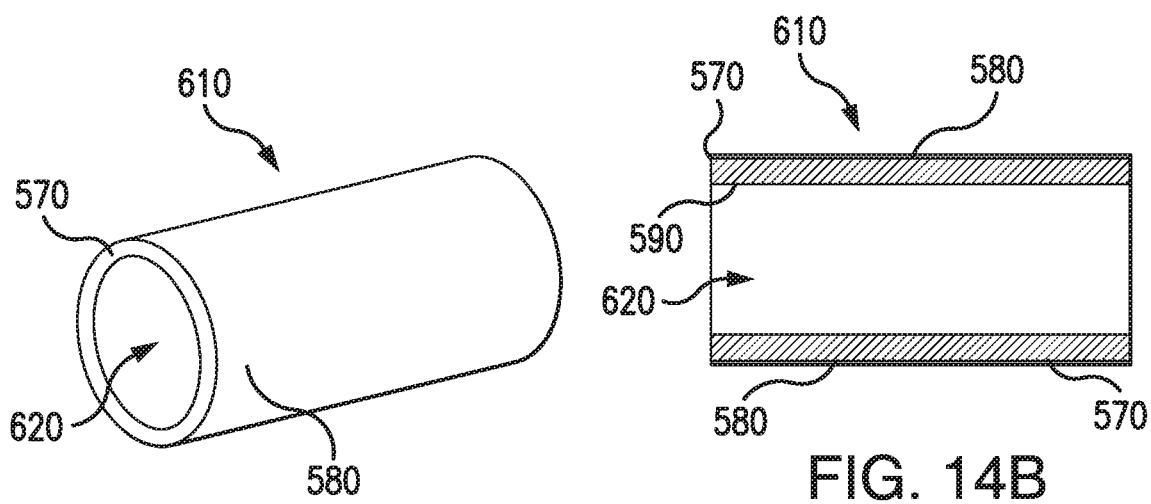
FIG. 14A
FIG. 14B
PRIOR ART

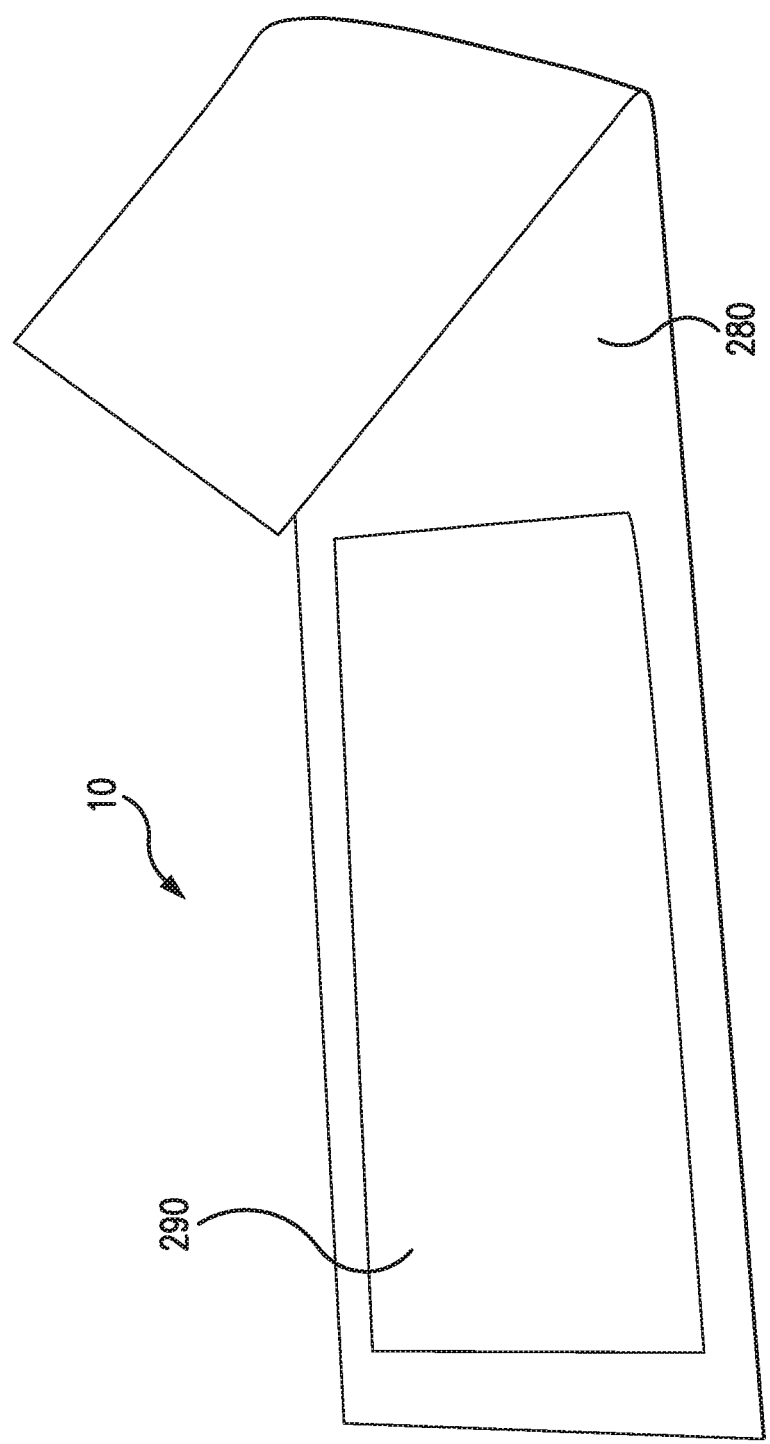

PHASE CHANGE MATERIAL FOR THERMAL THERAPY AND DELIVERY OF ACTIVE INGREDIENTS

CROSS-REFERENCE TO RELATED APPLICATIONS

This application is a continuation-in-part of U.S. application Ser. No. 14/602,893 entitled "Post-Surgical Articles for Reduction of Swelling, Edema, and Bruising" filed on Jan. 22, 2015, which claims priority to U.S. Provisional Patent Application No. 62/040,771 filed on Aug. 22, 2014, U.S. Provisional Patent Application No. 62/051,847 filed on Sep. 17, 2014, and U.S. Provisional Patent Application No. 62/062,372 filed on Oct. 10, 2014. This application also claims priority to U.S. Provisional Patent Application No. 62/364,998 filed on Jul. 21, 2016 entitled "Phase Change Material for Thermal Therapy and Delivery of Active Ingredients." The contents of each of the above-listed applications are hereby incorporated by reference herein in their entirety.

BACKGROUND OF THE INVENTION

Field of the Invention

The present invention relates to a field of thermal therapy articles employing a thermoplastic elastomer and more particularly to a thermoplastic elastomer composite having a high latent heat of fusion for the delivery of fat soluble active substances through the skin into the bloodstream.

Description of the Background Art

Following non-elective and elective surgical procedures, it is known that surgical sites and areas surrounding surgical sites bruise, swell, and often times have large amounts of localized edema due to the high amount of trauma incurred during these procedures. Although bruising, swelling, and edema naturally occur in response to trauma and are associated with natural, biological healing processes, excessive bruising, swelling, and edema may impede healing and, in certain instances, excessive bruising, swelling, and edema may even lead to post-surgical complications including, but not limited to, blood clot formation, embolism(s), and/or thrombosis.

Various types of post-surgical garments are currently used to treat surgical sites in an attempt to reduce bruising, swelling, and edema sometime associated with surgery. For example, most post-surgical garments (e.g., compression garments) utilize only fabric and/or hydrogels, which are used in an attempt to reduce and/or prevent post-surgical bruising, swelling, and edema. Post-surgical garments that incorporate thermal therapy devices often utilize hydrogels because they are relatively inexpensive, easy to manufacture, and may be easily adapted for the purposes of compression therapy, thermal therapy, cold compression therapy, or any combination thereof.

Although conventional post-surgical procedures utilize hydrogel compression garments, numerous problems exist with these compression garments. First, hydrogels (i.e., water-based gels) have a high heat capacity and high thermal conductivity due to their high water content, which means that these gels draw heat very quickly due to their high thermal conductivity and for a long time due to their high heat capacity. When use during thermal therapy and cold compressive therapy, the hydrogel's high heat capacity and high thermal conductivity may create an initial and maintained shock at an application site because the hydrogel tends to draw heat very quickly and for a very long time at the application site. Because of hydrogel's high thermal conductivity a patient may experience much discomfort, including damaged skin and/or additional tissue(s), when a hydrogel based compression garment is applied to a post-surgical site for purposes of thermal therapy or compression therapy. Second, hydrogels and hydrogel based compression garments typically lack adequate stretching properties to evenly distribute compressive forces around the surgical site, which disadvantageously leads to reduced treatment efficacy. For example, these uneven compressive forces result in random application of high compressive pressure and low compressive pressure around a surgical site. Areas receiving too much pressure (i.e., sites having high compressive pressure) often result in patient discomfort and potentially diminished vascular function, which may further lead to skin damage and other tissue damage around the surgical site. Areas receiving too little pressure may lead to edema micro-pooling at the surgical site, which may subsequently lead to delayed healing and/or further tissue damage. Third, hydrogels often lack durability because of the high water content within these materials. Specifically, these hydrogels lack tear strength due to high water content, which makes them prone to tearing during handling and application. Hydrogels also tend to desiccate very quickly during usage. Thus, for at least the above discussed reasons, hydrogels and hydrogel garments (including hydrogel compression garments) have very short lifespans for usage coupled with undesirable treatment results.

An alternative is to use thermoplastic. A well-known characteristic of thermoplastics is that they become soft and formable when heated. The majority of commonly used thermoplastics require higher temperatures than would be acceptable for contact with human skin, specifically the facial skin. To take advantage of the latent heat of fusion plastics must, at a minimum, reach the glass transition temperature which is far higher than what is acceptable for human skin contact. At the glass transition temperature, the plastic is able to utilize the latent heat of fusion and thermoplastics formability feature.

Alternatives exist such as the invention found in U.S. Pat. No. 5,565,132 which discloses a composite thermoplastic elastomer made of a polyolefin and phase change material in the form of a crystalline alkyl hydrocarbon. Advantageously, this invention provides formability and heat modulating properties but does not possess stretch characteristics that allow full return beyond a minimal percentage.

Publication US2014/0242127 discloses an invention that utilizes phase change materials in conjunction with other ingredients for application to the skin for regulation of heat. The phase change material of this invention is a salt and is encapsulated by one of variously described materials. The compound is then used in combination with a "cosmetically compatible carrier" and applied to the skin. This invention is used as a composition which does not afford the advantage being removable or re-usable after the initial application.

U.S. Pat. No. 9,249,303 discloses an invention that is a thermoplastic elastomer with phase change characteristics for providing heat to or absorbing heat from a body. An embodiment of this invention includes a percentage of a plasticizing oil in an amount of less than or equal to 45 percent by weight. It has been found that amounts greater than 45 percent by weight of the plasticizing oil are necessary to control the rate of delivery through the dermis. To maintain a higher percentage of fat soluble active ingredients a higher percentage of plasticizing oil must also be present.

Additionally, various methods exist for delivering active substances into the bloodstream. Common methods include intravenous injection, oral and rectal administration, and transdermal. Each of these methods had advantages and disadvantages. The present invention relates to a matrix comprised of a thermoplastic elastomer for controlled delivery of fat soluble active substances through the skin into the blood stream.

Numerous transdermal therapeutic systems (TTS) exist that attempt to provide controlled delivery of active substances. Disclosed in Brooke U.S. Pat. No. 6,328,992, Cannabinoid Patch and Method for *Cannabis* Transdermal Delivery, the invention is comprised of a reservoir that contains the active substance. Upon activation, active substance held within the reservoir begins to pass through various layers until it is in contact with the skin. Disclosed in Kydonie U.S. Pat. No. 9,050,348, Dermal Delivery Device, the invention is composed of a variety of layers, comprised of differing density materials containing the active substance. Each material acts as a matrix to suspend the active substance. Disclosed in Cleary, U.S. Pat. No. 5,006,342, Resilient Transdermal Drug Delivery Device, a plurality of layers infused with glycol based substances act as the mechanism for controlling the rate of active substance to the patient. Each invention has inherent complexities in the delivery systems that inhibit the storage and/or controlled release of the active substance. Therefore a device is needed that is able to store or suspend active substances until and then provide a controlled rate of delivery at a concentration level adequate for use.

As explained in a publication by Chang W. Song et al., which can be accessed at https://www.ncbi.nlm.nih.gov/pubmed/2808037, heat can be used for skin microcirculation in volar aspect on human skin. Red cell flow can increase up to 10-15 times the flow rate at room temperature. Similarly, heat therapy can be used in diabetic dermopathy to increase blood flow levels. Indeed, as seen in the chart below, blood flow levels increase as temperature rises.

In our prior art invention, a thermoplastic elastomer was used to control microbial activity and is reflected in U.S. Pat. No. 7,709,570 entitled "Surface Modification of Triblock Copolymer Elastomers", the disclosure of which is hereby incorporated by reference herein. The present invention represents an improvement over these types of prior art elastomers to better allow for the use of active substances such as antioxidants and antibiotics due to heat degradation.

More particularly, FIGS. 1-20C illustrate the elastomer of our prior invention. Referring to FIG. 1, thermoplastic elastomers having improved surface characteristics comprised a mixture 50 of one or more polymers, preferably triblock copolymers 40, a plasticizing agent or oil 30, and one or more additives 20. Suitable elastomeric materials included, for example, styrenic triblock copolymers, such as a hydrogenated poly(styrene-b-isoprene), a hydrogenated poly(styrene-b-isoprene-b-styrene), a hydrogenated poly(styrene-b-butadiene-b-styrene), a hydrogenated poly(styrene-b-isoprene/butadiene-b-styrene), or combinations thereof. In certain embodiments, elastomeric articles of the present invention comprised any of polystyrene-b-poly(ethylene/propylene) (SEP), polystyrene-b-poly(ethylene/propylene)-b-polystyrene (SEPS), polystyrene-b-poly(ethylene/butylene)-b-polystyrene (SEBS), or polystyrene-b-poly(ethylene-ethylene/propylene)-b-polystyrene (SEEPS), or any combination thereof.

Suitable plasticizing agents 30 included plasticizing oils such as paraffinic oils, naphtenic petroleum oils, mineral oils, and synthetic liquid oligomers of polybutene, polypropylene, polyterpene, etc. Optionally, a seeding of the oil was also effected, with an insoluble fine powder such as talc. In some embodiments, 300 to 1000 parts by weight of the plasticizing oil was used, more preferably between about 500 and 700 parts per hundred (PPH) of triblock copolymer.

The oil 30 or other plasticizing agent (also referred to herein as a plasticizer) was added to the triblock copolymer 40 in order to provide desired mechanical properties, such as elasticity, softness (or hardness), and elongation, tear and tensile strength characteristics of the resulting elastomer. For example, in some embodiments, suitable mechanical properties of the resulting elastomer included: (a) hardness between approximately 10 to 70 durometer on the Shore 00 scale, more preferably about 25 durometer on the Shore 00 scale; (b) ultimate elongation of approximately 300 to 2000 percent, more preferably about 1500 percent; and/or (c) tensile modulus at 300 percent elongation of between about 5 to 300 psi, more preferably about 30 psi.

One or more other additives 20 were also included, that precipitated out of a molten mixture of the polymer, plasticizing oil, and additive, upon cooling, thereby forming microcraters on the surface of the resulting thermoplastic elastomer. Preferably, the surface microcraters had an average radius of between about 0.001 mm and 0.07 mm, more preferably between about 0.0067 mm and 0.0433 mm, and an average depth between about 0.0183 mm and 0.1434 mm, for example to provide a desired tactile feel, and/or to optimize surface characteristics, mechanical properties or other characteristics of the resulting thermoplastic elastomer. The additive was a compound that has lower solubility in the mixture of polymer and plasticizing oil when cooled to room temperature (e.g., about 25° C.), than at the higher than room temperature at which the mixture of polymer and plasticizing oil and additive are all in solution. In preferred embodiments, additives 20 comprised one or more antioxidants and/or antimicrobial agents.

Table 1 included examples of suitable antioxidant additives.

TABLE 1

| Antioxidant Additives | Chemical Name |
|---|---|
| 1 | Tetrakis (2,4-di-tert-butylphenyl) [1,1-biphenyl]-4,4'-diylbisphosphonite |
| 2 | Tris (2,4-di-(tert)-butylphenyl) phosphite [e.g., IRGAFOS 168, Ciba Chemicals, Inc., Tarrytown, NY] |
| 3 | Butanedioic acid, dimethylester, polymer with 4-hydroxy-2,2,6,6-tetramethyl-1-piperidine ethanol |
| 4 | 2,6-di-tert-butyl-4-(4,6-bis(octylthio)-1,3,5-triazin-2-ylamino) phenol |
| 5 | 3,3',3',5,5',5'-hexa-tert-butyl-a,a',a'-(mesitylene-2,4,6-triyl) tri-p-cresol |
| 6 | Pentaerythritol Tetrakis (3-(3,5-di-tert-butyl-4-hydroxphenyl)propionate) [e.g., IRGANOX 1010, Ciba Chemicals, Inc., Tarrytown, NY] |
| 7 | Phenol, 2-(5-chloro-2H-benzotriazole-2-yl)-6-(1,1-dimethylethyl)-4-methyl |
| 8 | Thiodiethylene bis(3-(3,5-di-tert-butyl-4-hydroxyphenyl)propionate) |
| 9 | Calcium phosphonate |
| 10 | Dioctadecyl 3,3'-thiodipropionate |
| 11 | Didodecyl 3,3'-thiodipropionate |
| 12 | 2-(1,1-dimethylethyl)-6-[[3-(1,1-dimethylethyl)-2-hydroxy-5-methylphenyl]methyl-4-methylphenyl arctylate |
| 13 | N,N'-hexane-1,6-diylbis(3-(3,5-di-tert-butyl-4-hydroxyphenylpropionamide)) |

The tris (2,4-ditert-butylphenyl) phosphate as listed in Table I is a white crystalline powder, commonly used as a phosphate processing stabilizer for polycarbonate and polyolefins. It was used in combination with phenolic antioxidants and acts for synergistical color stability and polymer viscosity. The butanedionic acid as listed in Table I, also known as succinic acid, is a dicarboxylic acid with four carbon atoms, occurs naturally in plant and animal tissues and can play a role in intermediary metabolism (Krebs cycle). It is a colorless crystalline solid with a melting point of 185-187° C., soluble in water, slightly dissolved in ethanol, ether, acetone and glycerine, but not dissolved in benzene, carbon sulfide, carbon tetrachloride and oil ether. A common method of synthesis of succinic acid is the catalytic hydrogenation of maleic acid or its anhydride. Succinic acid has uses in certain drug compounds, in agricultural and food production, and in perfume esters. In a preferred embodiment, pentaerythritol tetrakis(3-(3,5-di-tert-butyl-4-hydroxphenyl)propionate) was the additive used.

In some embodiments of the prior invention, 0.5 to 10 parts per hundred (PPH) of one or more additives was mixed with the plasticizing oil or with the plasticizing oil and polymer mixture. More preferably, additive 20 was used in an amount of 0.45%-0.7%, based upon the total weights of polymer 40 plus mineral oil 30 plus additive 20. Using a percent may be more preferably to parts, or PPH, as the ratio of oil to polymer can change considerably. The additives were solid at room temperature (25° C.) and soluble in the molten mixture. The additives had higher solubility in the triblock copolymer elastomers at higher temperatures than at room temperature. The addition of such additives were in a predetermined proportion that exceeds the solubility of the additives 20 in the elastomer at room temperature. The addition of such additives to the mixture 50 of polymers 40 and plasticizing oil 30 was made either prior to the melting of the mixture in a heated vessel or when the mixture was in its molten state.

In previous embodiments of our invention where the additive comprised an antimicrobial agent, suitable antimicrobial agent additives included but were not limited to silver zeolite, silver zirconium phosphate, silver nitrate, silver thiosulfate, silver sulphadiazine, silver fusidate, and quaternary ammonium compounds (QAC). Other classes of silver-based antimicrobial agents were used as well, for example a silver acetate, a silver bromide, a silver carbonate, a silver chlorate, a silver chloride, a silver citrate, a silver fluoride, a silver iodate, a silver lactate, a silver nitrate, a silver nitrite, a silver perchlorate or a silver sulfide. One or more other antimicrobial agents were used in conjunction with or instead of such silver-based antimicrobial agents or other additive.

Modulus of elasticity, measured at 300% elongation, for the softer formulations of this elastomer were generally in the range of about 5 psi to 50 psi, exhibiting elongations at break in the range of 1500% to 2500%. The modulus of elasticity for a material is the ratio between the force required to stretch the material to a given length (represented as a percentage of its original length) and the cross section of the material prior to stretching. For example, the force required for 0% elongation is 0, values increase in substantially linear relation as force is applied to any given material. Accordingly, the higher the modulus the stiffer the material. The modulus is inversely proportional to the amount of plasticizing oil in the composition of the elastomeric gel.

Referring again to FIG. 1 of our prior invention, a method of making a thermoplastic elastomer according to an embodiment included mixing additive 20, plasticizing oil 30 and polymer 40 to form a mixture 50. One or more additives such as antioxidant or hydroxyl scavenger additives, e.g., such as one or more of those additives listed in Table I above, were used to create a powder-like precipitate that diffused to the surface of the elastomer during and/or after formation to create surface microcraters that reduced tackiness of the elastomer where such surface characteristics were desired.

Plasticizing oil 30 was heated prior to the addition of polymer 40 and/or additive 20. Mixture 50 was melted, for example in an extruder, a molding machine or other suitable heated vessel so that the additives became soluble in molten mixture 50 and remained in stable solution in the molten mixture 50.

Molten mixture 50 was then molded 60 or otherwise shaped into any desired shape or form 70, for example into a prosthetic sleeve or liner configured to receive the residual limb on an amputee (e.g., of an arm or leg) or a front or rear prosthetic breast skin, or a mask. When allowed to cool, the mixture solidified and form elastomer 80. The additives began to diffuse to the surface of elastomer 80 upon completion of the solidification process. Precipitation optionally was initiated by seeding the surface of elastomer 80 with fine powder 90 such as talcum powder, for example during the cooling process. Elastomer 80 was then cooled to make solidified elastomer 100, whereby additive 20 optionally precipitated to the surface of solidified elastomer 100, e.g., in the form of a dry powder.

If the plasticizing oil was heated, an appropriate temperature range was about 130 to 165° F. As described above, plasticizing oils such as paraffinic oils, naphtenic petroleum oils, mineral oils, and synthetic liquid oligomers of polybutene, polypropylene, polyterpene, and the like were used. Optionally, a seeding of the oil was also effected, with an insoluble fine powder such as talcum powder. Preferably, 300 to 1000 parts by weight, more preferably 500 to 700 parts per weight, of the plasticizing oil was disclosed.

An additive 20 was then be mixed in the plasticizing oil, optionally with seed, for a defined time, e.g., approximately 5 to 15 minutes, more preferably about 10 minutes, at a temperature of approximately 130 to 165° F. One or more additives 20 was optionally also added to the plasticizing oil 30 with or after the addition of the polymer 40.

In a specific embodiment of our prior invention, a polymer 40 or mixture of polymers was added to the plasticizing oil 30 or to the mixture of plasticizing oil and additives for a desired period of time, for example 20-40 minutes, more preferably about 30 minutes, at 130° F. to 165° F. starting temperature. As described in the prior invention, suitable polymers included any triblock copolymer, including for example styrenic triblock copolymers such as SEP, SEPS, SEBS or SEEPS. Preferably, 100 parts by weight of one or a mixture of two or more of a hydrogenated styrene/isoprene/butadiene block copolymer were used.

The mixture containing the plasticizing oil, the additive and the polymer was melted in an extruder, a reciprocating screw molding machine, or a heated vessel at about 400 to 460° F., more preferably between about 415° F., as an example in our prior invention. As mentioned, the additive was added to the mixture of polymers and plasticizing oils either prior to the melting of the mixture or in the melt phase.

After melting, the mixture was maintained at an elevated temperature, with or without mixing, for an amount of time necessary to ensure adequate dissolution and dispersion of the additives in the mixture. The time required to effect an adequate mixture was function of the triblock copolymer used and the equipment used to melt the mixture. For high molecular weight copolymers, such as Septon 4055 the time at temperature is considerably higher than for lower molecular weight copolymer such as Septon 4033. Also reciprocating screw type injection molding machines or plastic extruders require less time at temperature than melting pots or vats. Also, when using melting pots and vats the time at temperature can be dependent on the size of the pot. Thus, in some embodiments of the prior invention utilizing high molecular weight polymers, a typical time for processing the mixture was, for example, 10 to 30 minutes in a reciprocating screw type injection molding machine or an extruder, and 4 to 16 hours in a melting pot or vat. In embodiments utilizing low molecular weight polymers, a typical time for processing the mixture was, for example, 5 to 15 minutes in a reciprocating screw, and 2 to 8 hours in a melting pot or vat.

After the expiration of such amount of time, the mixture was molded or extruded or cast and then allowed to cool or was actively cooled. In either event, the mixture could have undergone a phase change from liquid to semi-solid or solid. The additives remained dissolved in the molten mixture, where upon solidification of the mixture, the mixture became an elastomer and precipitation of the additives from the elastomer began.

More particularly, where the mixture was first melted and then cooled, at a controlled temperature profile, precipitation of the additives occurred within the elastomer as the solubility parameters of the additive in the elastomer were exceeded. The solubility of the additives decreased as the temperature of the elastomer falls. Precipitation was optionally initiated by seeding the surface of the elastomer with a fine powder such as talcum powder. Precipitation was also initiated or facilitated by mechanical solicitation of the elastomer, such as stretching or other deformation of the elastomer. In a specific embodiment of our prior invention, placing the elastomer at room temperature allowed sufficient cooling to form microcraters of the desired size; and precipitation was also initiated by deforming or mechanically stressing (e.g., rubbing, stretching, bending) the elastomer at room temperature, e.g., after contacting it with a precipitation seed such as talcum powder.

The size of the particles of the precipitated phase was a function of the time temperature profile maintained during the cooling period and of the mechanical stress to which the elastomer was subjected. More particularly, the particles increased in size as the cooling rate decreased and as the amount of mechanical deformation decreased. A faster cooling rate (e.g., under refrigeration instead of room temperature) and greater mechanical deformation can produce smaller particle sizes.

The diffusion rate of precipitate to the surface of the liner also increased as the stress to strain ratio decreased, i.e., the diffusion rate increased as the modulus of the elastomer, or elastic limit stress, decreased.

Molding, casting or extruding of the molten mixture was conducted at a mold temperature of, for example, 95-130° F. for 5-10 minutes. The molded elastomer was removed from the mold after the expiration of such period of time. Although stretching was not required, stretching of the elastomer by about 50% improved the diffusion rate. Other mechanical deformation of the elastomer may be substituted for or added to the stretching.

The step of aging at a controlled temperature profile was also performed in the prior invention. For example, such aging was accomplished at a temperature of 20-32° C. for one (1) hour to 48 hours, more preferably about 24 hours. For example, FIG. 5 of the prior invention shows a photograph of an elastomer before (left) and after (right) aging at room temperature, e.g., approximately 25° C. for 24 hours.

The precipitated phase can diffuse to the surface of the elastomer and collect as a powder on its surface as shown in the right photo of FIG. 5. After optional removal of the surface powder, by wiping, washing (e.g., using a washing machine), or the like, additional powder can migrate to the surface of the elastomer. The process can be repeated until the saturation level at room temperature of the precipitate phase in the elastomer is reached. The process of diffusion to the surface may then stop.

As illustrated in FIG. 2 of the prior invention, the diffusion had several advantageous characteristics. The diffused precipitated phase modified the surface characteristics of elastomer 100 by creating micro-craters 120 on elastomer surface 110. The average number of microcraters per unit varied depending upon, for example, by the amount of antioxidant additives that are used, the speed of cooling, and/or by imparting mechanical stresses on the elastomeric material during the cooling process. When the precipitation occurred quickly, the microcraters were more numerous, smaller and more packed. When the particles fell out of solution slowly, the microcraters were larger and more spaced. If the process of precipitation of the hydroxyl scavengers occurred too slowly, the scavengers coagulated together to form crystals on the surface of the elastomer. The crystals and/or the resulting microcraters made the surface rough and were undesirable for use in skin contact applications.

The depth of the microcraters varied with the number and size of particles that emerged from the precipitation. The precipitated and migrated particles stacked on top of each other at the surface of the elastomer, forming a variable depth. The range of depth of surfaces having desirable characteristics were, for example, 0.005 mm to 0.2 mm, more preferably between about 0.018 mm and 0.143 mm.

The diffusion had several advantageous characteristics. The diffused precipitated phase modified the surface characteristics of the elastomers by creating micro-craters on the surface as seen in the photographs of FIGS. 6-12. Referring to FIG. 6, a cross sectional photograph at 60× magnification shows elastomer 80 with precipitated hydroxyl scavenger additives 770 forming in the gel medium, and microcraters 780 at the surface 110 of the elastomer. The precipitated additives 770 moved through the elastomer 80, creating microcraters 780 on surface 110. Therefore, the size of microcraters 780 is approximately equal to the size of the precipitated additive particles 770.

FIG. 7 shows the surface of a cooled elastomer 80 that was formed according to the present invention and which includes hydroxyl scavengers tightly packed and relatively small in diameter. As stated above, the size of the scavenger precipitation spots is equal to the size of the craters. FIG. 8 is a similar top-view photograph of another elastomer 80 formed as described above, showing hydroxyl scavengers having larger diameters and more spaces in between.

The amount of microcraters in each of the formed elastomers 80 was measured using a computer software as shown in FIG. 9. (Microscope. Skope by Boreal, Model 57900-01 with Motic DS-300 with 05×+PC camera; Software: Motic Diagro 2000, Motic China Group Ltd.) In particular, a box 790-1 and 790-2 was used to define an area, and the number of microcraters 800 in each area were counted. The following Table 4 shows the results of this procedure for the elastomer shown in FIG. 9.

FIG. 10 shows a top view photograph of an elastomer 80 formed as described above, but where the process of precipitation of the hydroxyl scavengers was allowed to occurred slowly as no seeding, stretching, or other manipulations to facilitate precipitation were performed. In this example, the scavengers coagulated together to form crystals on the surface of the elastomer. The crystals made the surface rough, which is undesirable for use in some skin contact applications. The scavenger particle sizes in this example were 3 to 19 times larger than those on a more desirable surface, such as those shown in FIGS. 7-9. Such size measurements were performed, for example, using a computer program to draw an a circle, ellipse, or other shape around the outline of each crystal or crater, and to calculate the area, perimeter and radius of the defined area.

As shown in FIG. 11, similar area, perimeter, and radius measurements were made for other elastomers such as elastomer 80. Referring to FIG. 12, the depth of the microcraters and hydroxyl scavengers 810 on the surface 110 of a thermoplastic elastomer 80 formed as described above according to the present invention was measured at various positions on the surface 110 using lines 820 drawn with the computer software. In the example of FIG. 12, the mean measured depth was 0.0634 mm, maximum depth was 0.143 mm, minimum depth was 0.0183, and the standard deviation of depth measurements was 0.0408 mm.

The surface modifications achieved by the prior art method reduced the friction between the skin or other human tissue and the elastomer and increased the surface area of the elastomer's surface. Referring to FIG. 3 of the prior invention, epidermal tissue 130 having skin surface 140 abutted molded surface 110 whereby precipitated additive 20 reduced lateral movement friction. Thus, a lubricant was added to molded surface 110 and retained by micro-craters 120 prior to contact with epidermal tissue 130. This was an advantageous feature in applications such as burn patient treatment applications, scar reduction pads, wound care dressings, goggle frames, masks, headbands, orthotics, prosthetics, garments, urinary catheters, temporary implantations, and applications of cosmetics.

The surface modifications were beneficial when the surface is wet with water or other liquid fluids. The micro-craters collect small pools of liquid which, in turn, provide additional lubricity. This was advantageous in medical, personal care, and cosmetic care applications, for example.

The surface modification techniques disclosed herein were also harnessed to transport compounds beneficial to the skin or other human tissue to the surface of the elastomer providing therapeutic or cosmetic benefits to such skin or other issue. As shown in FIG. 4 of the prior invention, permeable tissue target 150 having tissue surface 160 abutted elastomer surface 110 wherein therapeutic compound 170 embedded in micro-craters 120 migrated through tissue surface 160 to deliver compound 170 to tissue target 150. Therapeutic compounds were applied to molded surface 110 and retained by the micro-craters 120 for contact with tissue target 150. Such compounds included, but were not limited to, vitamins, nutrients, antibiotics, antimicrobials, fungicides, cancer chemotherapeutics, and other drugs.

The elastomers of the prior art invention were able to be molded or extruded or thermoformed into various shapes and items such as prosthetic liners and sleeves, external breast prostheses, seals for CPAP (Continuous Positive Air Pressure) masks or other masks, headbands, burn treatment dressings, other wound care dressing sheets and pads, scar reduction pads, socks for diabetic feet, malleolus pads, metatarsal pads, shoe insoles, other orthotics, garments, catheters and balloons for catheters, temporary implantations, and applications of cosmetics.

The thermoplastic elastomers of the prior art invention included antioxidants and hydroxyl scavengers as additives, and are formed into useful articles for wound healing applications.

In some embodiments of the prior art invention, a thermoplastic elastomer included one or more antioxidant and/or hydroxyl scavenger additives, for example, Irganox 1010 and/or other additives such as those listed in Table 1 above. Such additives acted as effective scavengers of free radicals and hydroxyl groups, and had beneficial effects on the skin, including for example, wound healing. Antioxidant additives such as Irganox 1010 were previously used in thermoplastic polymers to scavenge oxygen and other free radicals that may degrade the polymers when they are in a molten state for molding and extrusion.

In the prior invention, an excessive amount of such antioxidants were utilized; for example in an amount beyond the solubility of the antioxidant in the thermoplastic elastomer. In the polymer at room temperature, this excess, over time, precipitated out of the bulk of the polymer. Specifically, in a thermoplastic elastomer comprising mineral oil and a styrenic triblock copolymer, Irganox 1010 was added in excess of its room temperature solubility in the gel, precipitated in the build of the polymer, then migrated to the surface of the gel. In some embodiments, the mineral oil also migrated to the surface of the gel and included the additive (e.g., Irganox 1010) dissolved within the oil. The mineral oil penetrated into the skin of the user and carried with it the Irganox 1010 and/or other additives. Such thermoplastic elastomers as described in the prior invention were used, for example, as liners or sleeves in prosthetic devices, as bandages, patches, pads, wound dressings, or in any other applications involving prolonged contact of an elastomer with the skin of a user, and in particular where healing of a wound is desired. The patient or user included human or non-human mammals, e.g., primate, dog, cat, mouse, cow, etc.

In preferred embodiments of our prior invention, the precipitated additives comprised antioxidants or free radical scavengers that are useful in treating different types of wounds, e.g., lesions due to burns, trauma, surgery, diabetic lesions or ulcers, pressure ulcers, etc. A therapeutic article such as a sleeve, liner, bandage, dressing, pad, malleolus pad, scar patch, insole or other article included a thermoplastic elastomer with one or more additives. A fabric or other backing was integrated within or bonded to the article. The fabric was stitched or woven, and in some embodiments was elastic in one or more directions and in other embodiments was substantially inelastic in one or more directions.

Examples of articles that include thermoplastic elastomer lining according to the prior art invention and that were used for wound healing or scar repair included prosthetic liners, a prosthetic sleeve, a prosthetic skin, a burn dressing, a scar reduction pad, a wound care dressings, goggle frames, a mask, a headband, an orthotic device, a garment, a catheter, a temporary implantation, and a cosmetic application.

As mentioned above, the thermoplastic elastomers of the present invention were particularly suitable for use as liners, sleeves or other skin contact points in a prosthetic device. For example, referring to FIG. 13 of the prior invention, a prosthetic liner 540 was configured to receive and fit against a residual limb of an amputee patient, and to hold a prosthetic limb against the residual limb. For example, liner 540 included a thermoplastic elastomer 570 with a fabric backing 580 attached to one side. An inner surface 590 of the thermoplastic elastomer preferably had microcraters as described and included antioxidants, hydroxyl scavengers, antimicrobials, lubricants or other agents or substances that were applied to surface 590 or precipitated from elastomer 570. An open end 550 was configured to receive the residual limb of the patient and a closed end 560 was configured to attach to a prosthetic limb or other device. An umbrella 600 or other device for securing the prosthetic limb was attached to or integrated within the liner 540.

The fabric 580 of liner 540 included any suitable fabric and may be stitched or woven. Fabric 580 preferably allowed stretching in a radial direction (e.g., radial stretching of up to 50%) and resisted elongation (e.g., relatively inelastic in a longitudinal or axial direction to support the weight of a prosthetic limb).

Referring to FIGS. 14A and 14B of the prior invention, a prosthetic sleeve 610 according to the present invention comprised a thermoplastic elastomer 570 surrounded by a sleeve fabric 580. The sleeve preferably was substantially cylindrical or conical in shape, and included a central passage 620 through which a limb or other body part was placed. When sleeve 610 was applied, inner surface 590 contacted against the skin of the user. In embodiments where therapeutic agents were included in elastomer, such agents were transferred, e.g., by direct contact with the skin or through absorption of oil in the elastomer (e.g., where the therapeutic agent was carried by the oil). As described, such sleeves or liners were used to treat various types of wounds and/or infections, depending upon the additives in the composition of the thermoplastic elastomer.

One skilled in the art appreciated that the thermoplastic elastomers of the prior invention could be employed in various arrangements of known prosthetic devices. For example, additional details and examples of liners with which the thermoplastic elastomers of the present invention may be used can be found in U.S. Pat. No. 6,454,812 to Laghi and U.S. Pat. No. 4,923,474 Klasson et al., each of which is incorporated by reference herein in its entirety.

The prior invention provided a method of treating or preventing infection at a site by contacting the site using a thermoplastic elastomer, wherein the additive comprised an antimicrobial agent. In preferred embodiments of the prior invention, a thermoplastic elastomer comprised silver-based antimicrobial agents, provides a moisture barrier by being impermeable to water, and in its softer formulations, distributes pressure evenly on the skin surface and virtually eliminates shear forces on the skin. Silver-based antimicrobial agents are more stable than other active ingredients at higher temperatures.

An elastomer comprising one or more antimicrobial agents can be applied, for example, to a wound to treat or prevent an infectious agent such as a bacterium, a virus, a parasite, or a fungus.

A thermoplastic elastomer was made as described above with respect to FIG. 1 of the prior invention, wherein the additive 20 comprised one or more antimicrobial agents. For example, referring to FIG. 15 of the prior invention, a process of making an elastomer included combining antimicrobial agent 630, plasticizing oil 640, and polymer 650 to form mixture 660. Heat 680 was applied to mixture 660. Plasticizing oil 640 was optionally heated prior to or after the addition of antimicrobial agent 630 and polymer 650. Mixture 660 was melted in an extruder, a molding machine or other suitable heated vessel so that the antimicrobial agent 630 became suspended in molten mixture 660 and remained in stable suspension in the molten mixture 660. Molten mixture 660 was molded 670 into the form of a useful item at an appropriate temperature. When allowed to cool, e.g., towards room temperature of approximately 25° C. the mixture solidified and formed elastomer 690. The antimicrobial agent 630 began to diffuse to the surface of the elastomer, preferably along with other microcrater-forming additives as described above with respect to FIG. 1. Upon completion of the solidification process, diffusion of the additives was facilitated by seeding with talcum powder and/or imparting mechanical stresses on the elastomer 690, as described above.

If the plasticizing oil was heated, an appropriate temperature range was about 130 to 165° F. Plasticizing oils such as paraffinic oils, naphtenic petroleum oils, mineral oils, and synthetic liquid oligomers of polybutene, polypropylene, polyterpene, and the like were optionally used. In some embodiments, 300 to 1,200 PPH of the plasticizing oil were used, more preferably between about 500 and 700 PPH.

The inert nature and antimicrobial efficiency of silver made it an attractive option for the prior invention. It is not toxic, flammable or corrosive and will not cause bacteria to become resistant to antibiotics. Silver stops bacteria or fungi degrading the object's physical properties, and also prevents the build-up of harmful bacteria, which can be a source of infection to humans. Microorganisms such as bacteria, fungi and algae can affect the aesthetic and physical properties of an elastomer by causing black spotting or discoloration, odor and polymer degradation. And in hospitals and care homes where patients are particularly vulnerable to infection, the buildup of bacteria such as methicillin-resistant *Staphylococcus aureus* (MRSA) can contribute to the spread of deadly infections.

An advantage of silver-based additives is that they can be used in high temperature processing. For example, silver zirconium phosphate is thermally stable up to 800° C. The anti-microbial agents are mixed either in the dry polymer or in the mixture of polymer and plasticizing oil in the prior invention. Other additives such as antibiotics cannot withstand the same temperature ranges as silver-based additives.

Silver-based antimicrobials use an ion exchange mechanism that slowly releases silver ions, which interact with the bonding sites on the microbe surface to prevent bacteria from reproducing. This slow, regulated release provides long-lasting effectiveness. In contrast, organic antimicrobials inhibit the growth of microbes by slowly leaching to the surface of the plastic, and subsequently into surrounding fluids. Such leaching can limit the durability of the additive and also cause discoloration and an unpleasant taste. In other embodiments, a quaternary ammonium compound (QAC) is used.

In some embodiments, approximately 100 parts by weight of triblock copolymer, 0.05 to 20 PPH of one or more antimicrobial agent, more preferably between about 0.25 and 20 PPH of antimicrobial agent, and 100 to 900 PPH of plasticizing oil, more preferably between about 500 and 700 PPH of plasticizing oil, were used. In some embodiments, an antioxidant was also added, for example about 2-4 parts of Irganox 1010, more preferably about 2.9-3.0 parts.

In other embodiments, an antimicrobial agent incorporated within a thermoplastic elastomer was a silver sodium hydrogen zirconium phosphate (e.g., AlphaSan RC 2000, Millken Chemical, Spartanburg, S.C.), which is a zirconium phosphate ion-exchange resin containing approximately 10% silver. In a preferred embodiment, AlphaSan RC 2000™ comprises approximately 0.5% to 5%, preferably between about 1% and 3%, more preferably about 2%, of the total weight of the polymer, plasticizer and additive formula. Optionally, a lubricant, ointment, or other substance was optionally added to the molded surface of the elastomer, and was retained within the microcraters on the surface of the elastomer as described above.

FIG. 16 illustrated the normal course of infection when conventional elastomers were used. As microbes 700 encountered a hospitable environment, such as skin 150, they began to colonize. Microbes 700 began to multiply and exponentially colonized the area 700a. In contrast, FIG. 17 shows that silver ions 710 slowly migrated from elastomer 110a toward tissue 150. The positive charge of silver ions 710 allowed the silver ions to bond to the surface of microbes 700, thus interrupting reproduction. Since microbes 700 cannot reproduce, they eventually died and infection was thereby avoided. The silver ions were not consumed or dissolved in this process and therefore are able to continue their effectiveness.

FIGS. 18-19 show an application of the prior invention. In FIG. 18, wound 730 was located at the knee area of an individual's leg 720. Molded surface 110 of thermoplastic elastomer contacted wound 730 whereby antimicrobial agent 710 migrated from molded surface 110 to wound 720. In addition, the moisture impermeable properties of thermoplastic elastomer kept the wound area from drying out. The molded surface 110 kept a predetermined pressure of on the wound to control edema and/or other disorders relating to pressure on tissue and wounds.

FIG. 19 illustrated the same principle but with a prosthetic socket 740 engaging leg 720 by liner 610 coated with thermoplastic elastomer on the inner surface of the fabric of the liner, in contact with wound 730. As the thermoplastic elastomer had all the properties of a prosthetic liner an additional advantage of the prior invention was to prevent, stem or cure infections caused by previously ill-fitted prosthetic devices. Wounds and subsequent infections occurred when a user was improperly fitted with a prosthetic device, the user improperly deployed the device or the user's body has changed since the prosthetic device was originally designed. The prior invention was used to treat and prevent further infections, reduce friction and stress on the tissue of a prosthesis wearer by incorporating the thermoplastic elastomer into a liner, sleeve or any other situation wherein a elastomeric surface must abut or compress against tissue. The present invention is used to treat and prevent diseases currently afflicting a prosthesis wearer or other user.

A case where antimicrobial thermoplastic elastomer for prosthetic liners was of particular advantage was that of post-operative prosthetic liners, as the opportunity for serious infections is more likely immediately after surgery when the surgical sutures are still fresh.

FIGS. 20A-20C of the prior invention show the effect of fitting a patient's limb having skin ulcers with a prosthetic liner (ALPS EasyLiner™, Alps South Corporation, St. Petersburg, Fla.). The liner comprised Septon 4055 and Carnation 70 mineral oil, and was supersaturated with Irganox 1010 to form microcraters according to the present invention.

Therefore, it is an object of this invention to provide an improvement which overcomes the aforementioned inadequacies of the prior art devices and provides an improvement which is a significant contribution to the advancement of the thermoplastic elastomer art.

Another object of this invention is to provide a thermoplastic elastomer that will not rupture or crumble under shearing stress conditions.

Another object of this invention is to provide a thermoplastic elastomer that will not tear under tensile conditions.

Another object of this invention is to provide a thermoplastic elastomer that will provide comfort against the skin when in contact with skin for extended periods of time.

Another object of this invention is to provide a thermoplastic elastomer where the surface characteristics of the elastomer are beneficial in skin contact applications.

Another object of this invention is to provide a thermoplastic elastomer which acts as a matrix to suspend an active substance.

Another object of this invention is to provide a thermoplastic elastomer for controlled delivery of fat soluble active substances.

Another object of this invention is to provide a thermoplastic elastomer which delivers an active substance into a user's bloodstream through the skin.

Another object of this invention is to provide a thermoplastic elastomer which allows the addition of the active substance at either the polymer phase, plasticizing oil phase, or after the elastomer has been molded.

These and other objects and advantages of this invention will become apparent upon reading the following specification and claims appended thereto.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

A need exists to provide garments having low thermal conductivity, relatively high latent heat of fusion, and high durability and resiliency when worn by a wearer. In certain aspects, these garments further include compression garments having the ability to provide evenly distributed compressive forces (e.g., a high modulus of elasticity). Disclosed herein are garments (e.g., compression garments) having low thermal conductivity, relatively high latent heat of fusion, and high durability and resiliency, which overcome the disadvantages associated with conventional hydrogels and hydrogel garments and compression garments. In certain aspects, the garments further include the ability to provide evenly distributed compressive forces (e.g., a high modulus of elasticity). Furthermore, these garments advantageously result in better patient comfort and overall improved healing processes due to the combination of any of the following features: (i) low thermal conductivity; (ii) relatively high latent heat of fusion; (iii) high durability and resiliency; and (iv) formability. In certain aspects, the disclosed garments include compression garments that evenly distribute compressive forces.

The disclosed garments may include a post-surgical treatment mask including a thermoformable assembly having a thermoplastic elastomer arranged with a fabric layer, the thermoformable assembly configured to be heated to a transition temperature of the thermoplastic elastomer such that the thermoformable assembly can be shaped to conform to contours of a user's face, and a styrene-based polymeric gel layer arranged on the thermoformable assembly. In certain aspects, the disclosed garments may include a post-surgical treatment mask including a thermoformable assembly configured to be heated to a transition temperature of the thermoplastic elastomer such that the thermoformable assembly can be shaped to conform to contours of a user's face, and a styrene-based polymeric gel layer arranged on the inner fabric layer. This thermoplastic elastomer should be configured to form a rigid structure that is capable of supporting and applying pressure to the gel when secured to the wearer.

The present invention overcomes the disadvantages of the current art and provides a durable elastomer having improved surface characteristics and enhanced utility in applications involving sustained contact with human skin. The invention is a thermoplastic elastomer comprising polymer, plasticizing oil, paraffin, antioxidant, and active ingredients for the application of heat to various parts of the body. Advantageously, the thermoplastic elastomer (TPE) changes phase at a temperature that is acceptable for skin contact. This allows for utilization of the latent heat of fusion that occurs at the phase change temperature. While being heated, the elastomer softens, becoming formable. The formable elastomer is then able to conform to the surface on which it is placed. This allows for an increase in surface area contact compared to other two dimensional articles that provide thermal therapy.

Heat therapy is used extensively by the medical and cosmetic community for assisting in the healing of various ailments and injuries. Thermal therapy invokes a response by the vascular system to improve blood flow to and from localized areas. The present invention utilizes plasticizing oil that is capable of storing lipid based active ingredients and then delivering them transdermally. In some embodiments, the active ingredients are absorbed into the elastomer in an application process after the manufacturing of the elastomer. In another embodiment, the active ingredients are applied to the user's skin and then the elastomer is applied to utilize the heat thereof. In either case, the presence of heat in the elastomer increases the transfer of the active ingredients through the dermis and into the blood stream. The plasticizing oil acts as a carrier of the fat soluble active ingredients. The elevated temperature of the thermoplastic elastomer also increases the rate at which the oil phase is exuded from the thermoplastic elastomer. The combination of the plasticizing oil and the temperature of the thermoplastic elastomer are used to modulate the rate of transdermal delivery of active ingredients.

In one embodiment, the thermoplastic elastomers of the invention have microcraters on their surface, formed by the precipitation of additives, such that the surface is smooth to the touch and low friction to the skin, but which provides a surface of increased surface area relative to surfaces without such microcraters. Such increased surface area provides unique advantages over prior art. For example, such a surface can incorporate increased amounts of therapeutic or antibiotic ingredients. The addition of these ingredients during the process of making the thermoplastic elastomer is sensitive and requires delicate timing and heating due to the heat sensitivity of the active ingredients contemplated for the present invention.

In some embodiments, thermoplastic elastomers of the present invention may be manufactured by mixing together oil, a polymer and one or more additives, e.g., an antioxidant, an antimicrobial agent, and/or other active ingredients, to form a mixture which is melted then cooled into the thermoplastic elastomer. Alternatively, the additives may be added to the mixture after the mixture is melted or during the cooling process. During cooling the thermoplastic elastomer may be molded or otherwise formed into any number of articles including, but not limited to, prosthetic liners, prosthetic sleeves, external breast prostheses, breast enhancement bladders, wound dressing sheets.

In some embodiments, the plasticizing oil is paraffinic or naphthenic. In other embodiments it may be vegetable oil. In still other embodiments it may be comprised of a mixture of any of the above mentioned oils.

In some embodiments, the polymer comprises a triblock copolymer comprising styrene and at least one of ethylene, butadiene, butylene, propylene, or isoprene, for example a styrene-ethylene-ethylene-propylene-styrene, a styrene-ethylene-butylene-styrene, or a styrene-ethylene-propylene-styrene. In certain embodiments, thermoplastic elastomers according to the present invention comprises a polymer that is a hydrogenated poly(styrene-b-isoprene), a hydrogenated poly(styrene-b-isoprene-b-styrene), a hydrogenated poly(styrene-b-butadiene-b-styrene), a hydrogenated poly(styrene-b-isoprene/butadiene-b-styrene), or combinations thereof. In certain embodiments, the thermoplastic article comprises any of polystyrene-b-poly(ethylene/propylene) (SEP), polystyrene-b-poly(ethylene/propylene)-b-polystyrene (SEPS), polystyrene-b-poly(ethylene/butylene)-b-polystyrene (SEBS), or polystyrene-b-poly(ethylene-ethylene/propylene)-b-polystyrene (SEEPS), or any combination thereof.

Thermoplastic elastomers of the present invention also comprise selected amount of one or more plasticizing oils, for example, a paraffinic oil, naphtenic oil, a mineral oil, or a synthetic liquid oligomer of a polybutene, a polypropene, or a polyterpene oil. The plasticizing oil may be heated prior to mixing the additive and polymer therewith, but such heating is not strictly necessary. An extruder, a molding machine, or other similar heated vessel is used to accomplish the above-mentioned melting of the mixture so that the additive(s) become melted and soluble in the molten mixture.

A thermoplastic elastomer comprises one or more additives, such as antioxidants or hydroxyl scavengers, that optimize the surface characteristic of the elastomer. Such additives may be in a stable solution with a mixture of polymer and plasticizing oil when the mixture is in its molten state. An elastomer is formed when the molten mixture cools and solidifies. As the mixture cools down the solubility of the additives decreases and the mixture becomes a supersaturated solution. When solidification is complete, the additives begin to precipitate from the elastomer. The additives migrate, for example through a process of diffusion, to the surface of the elastomer where they create microcraters, pits or other imperfections or features on the surface of the elastomer. The migrated additives may also form a dry layer of microscopic powder on the elastomer surface. The microcraters and/or the powdery interface may improve the comfort of the user and enables the elastomer to remain in contact with the user's skin for prolonged periods of time. Even if the surface is wet, the micro-craters may collect small pools of liquid that provide lubricity. In embodiments wherein the thermoplastic elastomer is used to promote wound healing, the additive is preferably an antioxidant or free radical scavenger.

In some embodiments, the outer layer fabric is made with a non-low melt polyester yarn, a non-low melt nylon yarn, a non-low melt polypropylene yarn, a non-low melt polyethylene yarn, cotton yarn, wool yarn, polyester, polypropylene, polyethylene, any combinations thereof, and the layer may either be multifilament or monofilament. In certain embodiments, the thermoplastic elastomer is removable. The preferably styrene-based gel is between 0.050 and 0.625 inches, and more preferably between 0.100 and 0.300 inches in thickness. The gel preferably has a thermal conductivity ranging from 0.05 to 3.00 W/mk.

The mask preferably includes a strap configured to secure around a user's head to hold the mask in place on the user's face.

In certain aspects, the mask includes hook and loop fasteners for securing the strap to the mask.

In certain aspects, the mask includes two straps configured to secure around a user's head to hold the mask in place on the user's face.

In certain aspects, the mask is a partial face mask adapted to cover a user's eyes and the bridge of the nose.

In another embodiment, the garment may include a post-surgical face mask made from a styrene-based gel shaped to conform to and cover a wearer's face including a chin, a nose, cheeks, forehead, and ears, the mask having openings at the wearer's eyes, nose, and mouth, and a strap configured to fasten around the forehead and under the chin to secure the mask in place.

A feature of the present invention is the refractive index is less than 2 at the phase change temperature. As a result, it is readily distinguishable when the phase change has occurred. This is an advantage over other devices that do not provide temperature feedback.

In a preferred embodiment, the active substance is added after the thermoplastic elastomer is formed. Active substances may be added to the polymer phase, plasticizing oil phase, or afterwards to the molded elastomer. Such active substances are included in Table 1 but are more broadly classified as any nonpolar substances. The active substances are preferably added after each phase has cooled as the preferred active substances are heat sensitive and can degrade in high temperatures. The improvement of the present invention over the prior invention is the addition of the active ingredient at lower temperatures to prevent degradation. The prior art used silver-based antimicrobials which could withstand higher temperatures. The present invention uses active ingredients which require lower temperatures in order to retain their effectiveness.

The present invention provides a composition for controlling active substances activity with skin contact applications and for treating wounds including a thermoplastic elastomer comprising a dispersion of antioxidants and/or antimicrobial agents within the thermoplastic elastomer. The thermoplastic elastomers may also have a predetermined modulus sufficient to maintain a substantially uniform pressure on a wound. Application of such a thermoplastic elastomer over a wound or the skin permits the migration of hydroxyl scavengers and/or antimicrobial agents and/or lipophilic substances from the surface of the elastomer to the skin. The presence of such compounds may aid in wound healing and/or keep the skin and wound site free of infection. The invention may preferably take the form of a mask for application to a user's face or an insert for insertion into a user's ear canal. The mask may or may not include an open or closed loop ring to either directly or indirectly provide a seal on the mask for respiration.

In other embodiments, thermoplastic elastomers of the present invention may be impermeable to water whereby retention of moisture to a wound and skin is achieved. The soft nature of the elastomer may enable controlled compression of the wound to prevent ischemia. The soft nature of the elastomer also minimizes frictional and shear forces on the skin. As a consequence tissue necrosis may be virtually eliminated.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, references should be had to the following detailed description taken in connection with the accompanying drawings in which:

FIG. 1-20C illustrate the prior art elastomer.

FIG. 31 is a garment according to another embodiment including the styrene based gel permanently positioned on an elongate, elastic application to a wearer's abdominal area.

FIG. 37(b) further shows a cross-section of this embodiment showing the outer layer and thermoplastic elastomer gel layer.

Similar reference characters refer to similar parts throughout the several views of the drawings.

DETAILED DESCRIPTION OF THE PREFERRED EMBODIMENT

Figure 1:
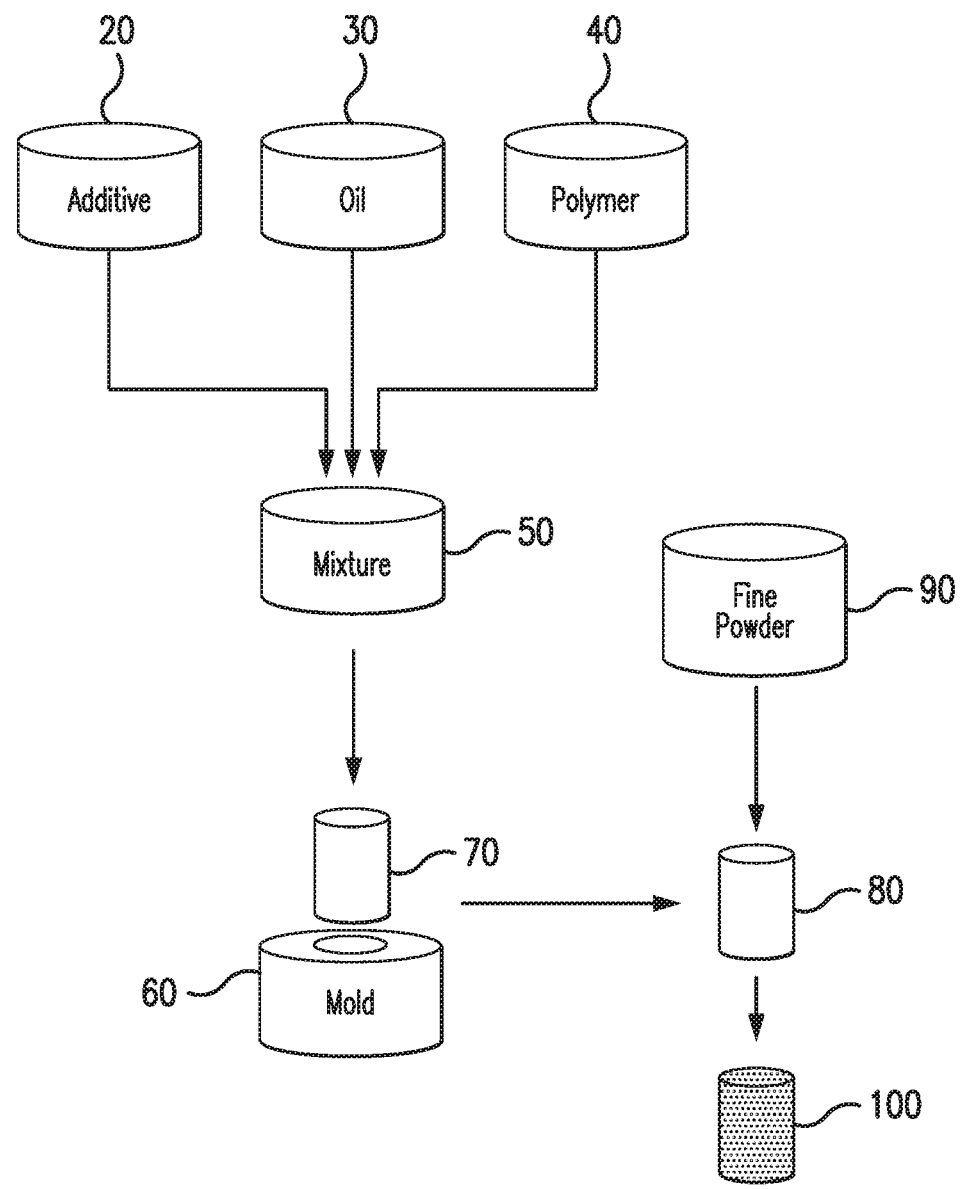
Figure 2:
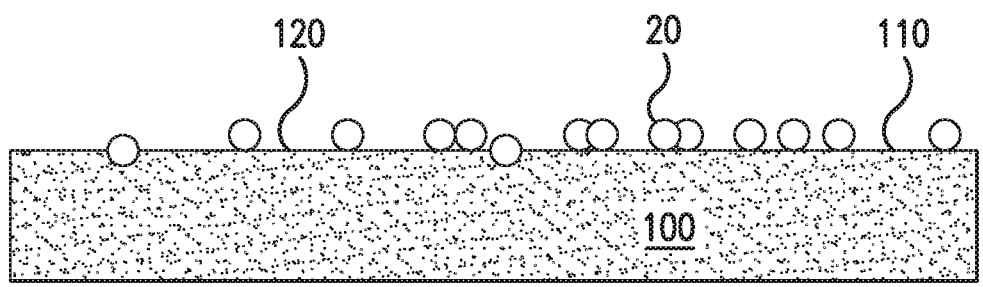
Figure 3:
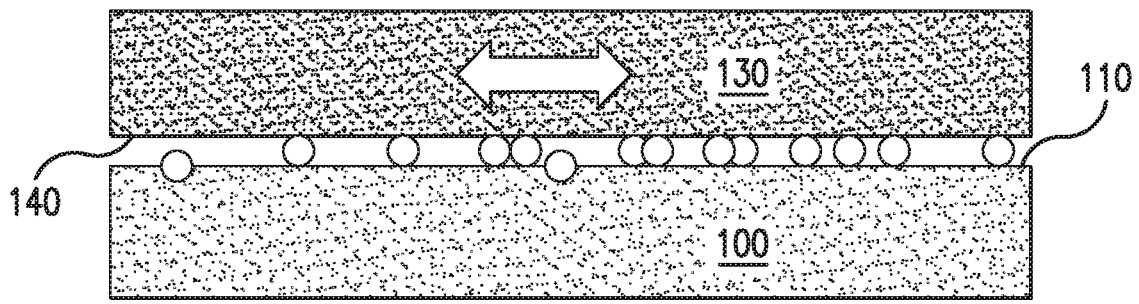
Figure 4:
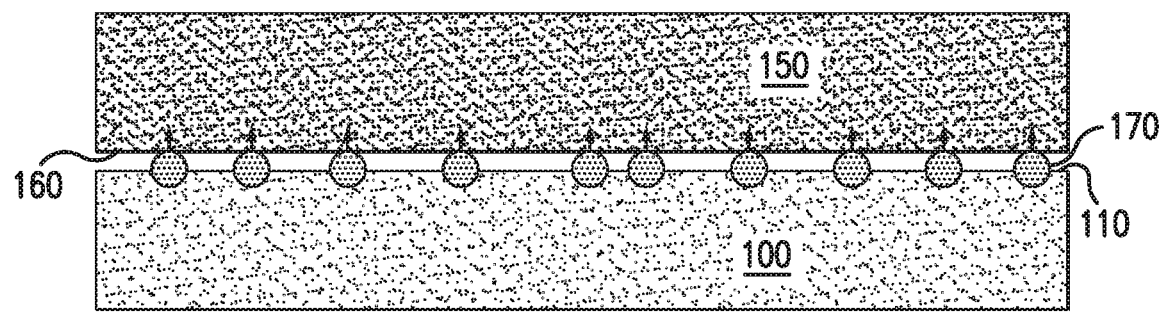
Figure 5:
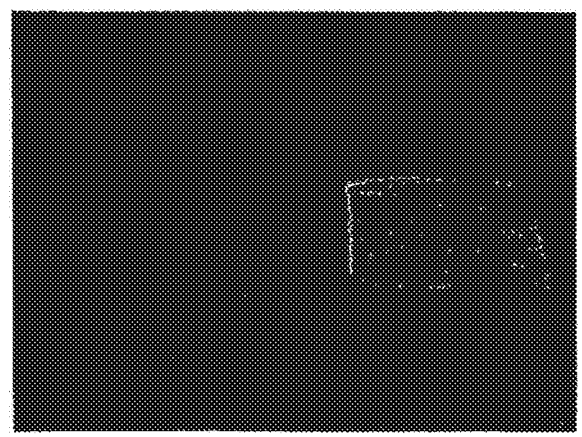
Figure 6:
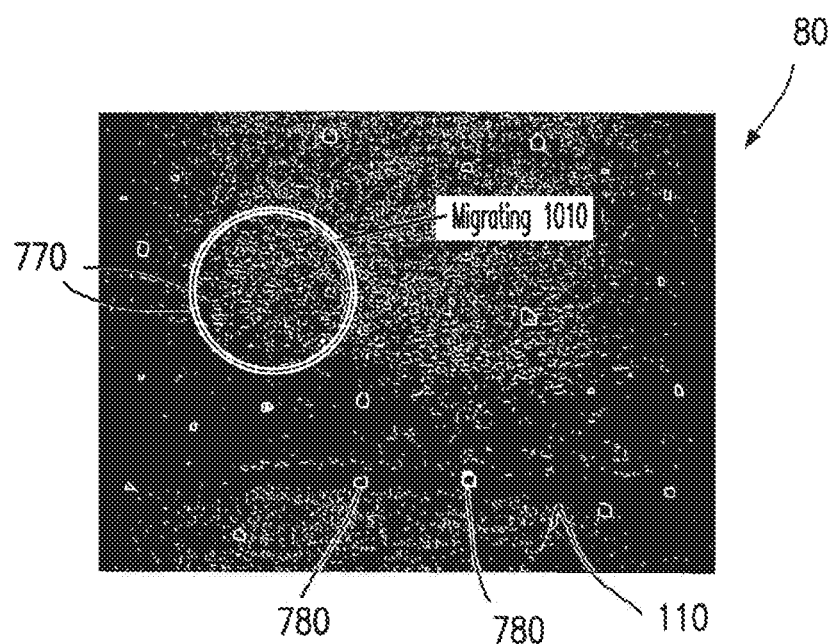
Figure 7:
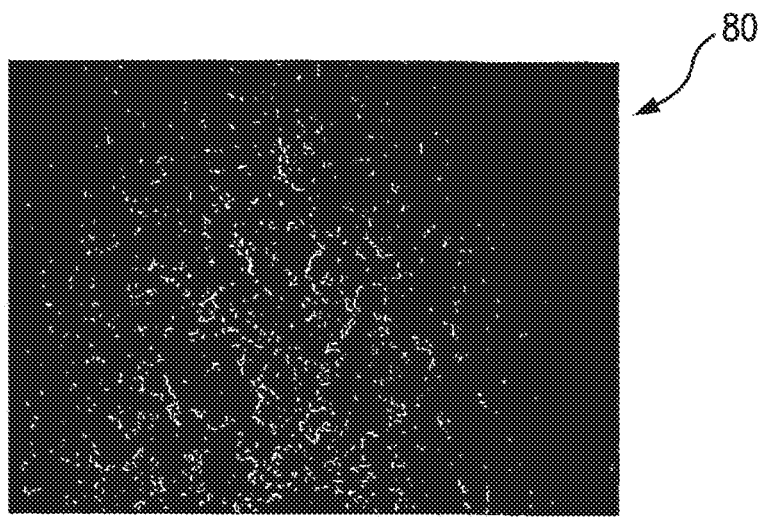
Figure 8:
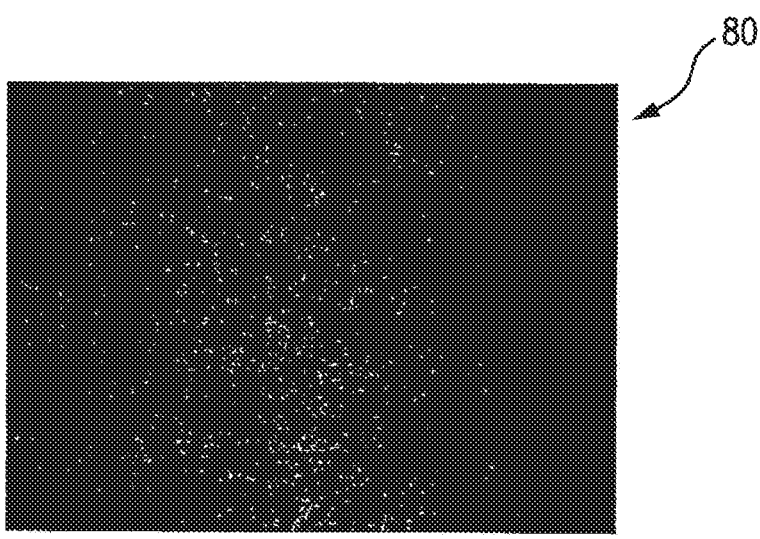
Figure 9:
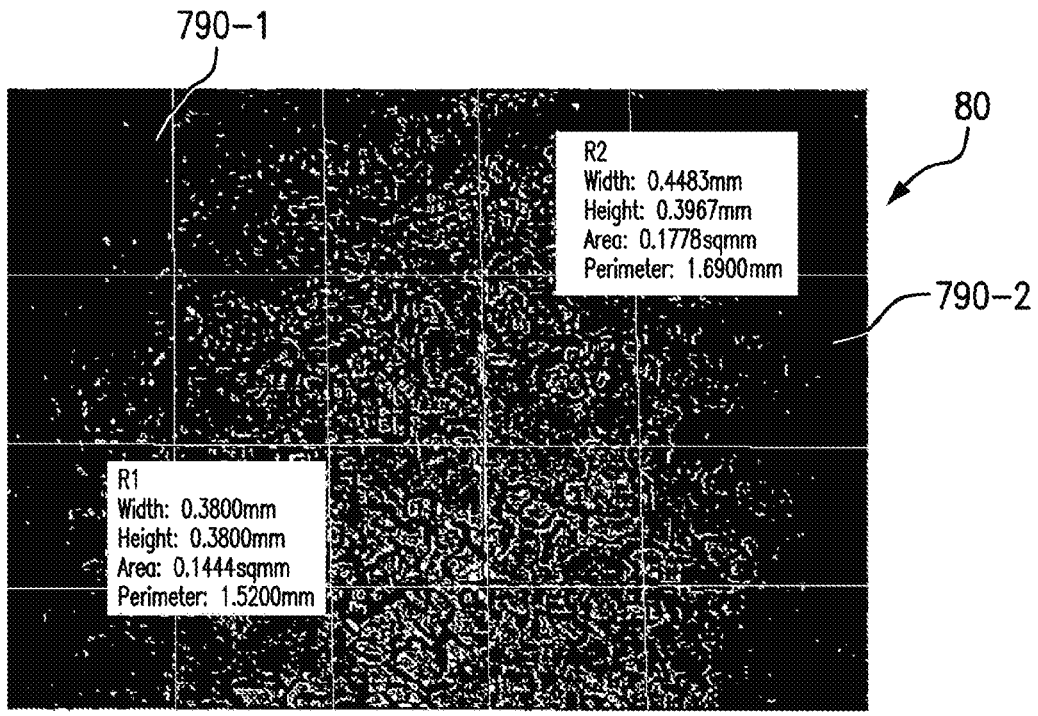
Figure 10:
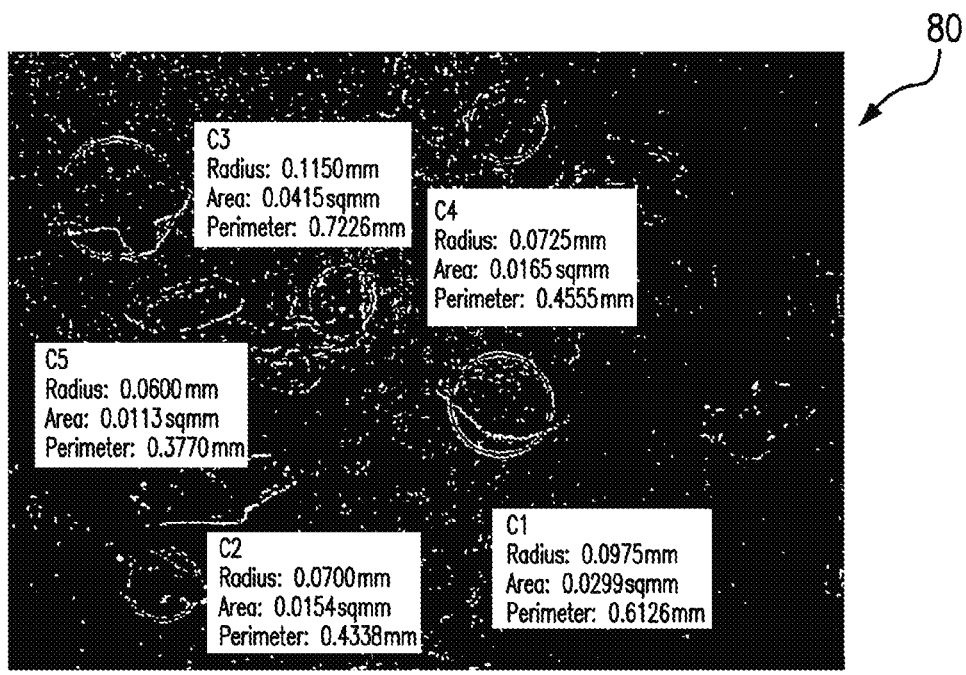
Figure 11:
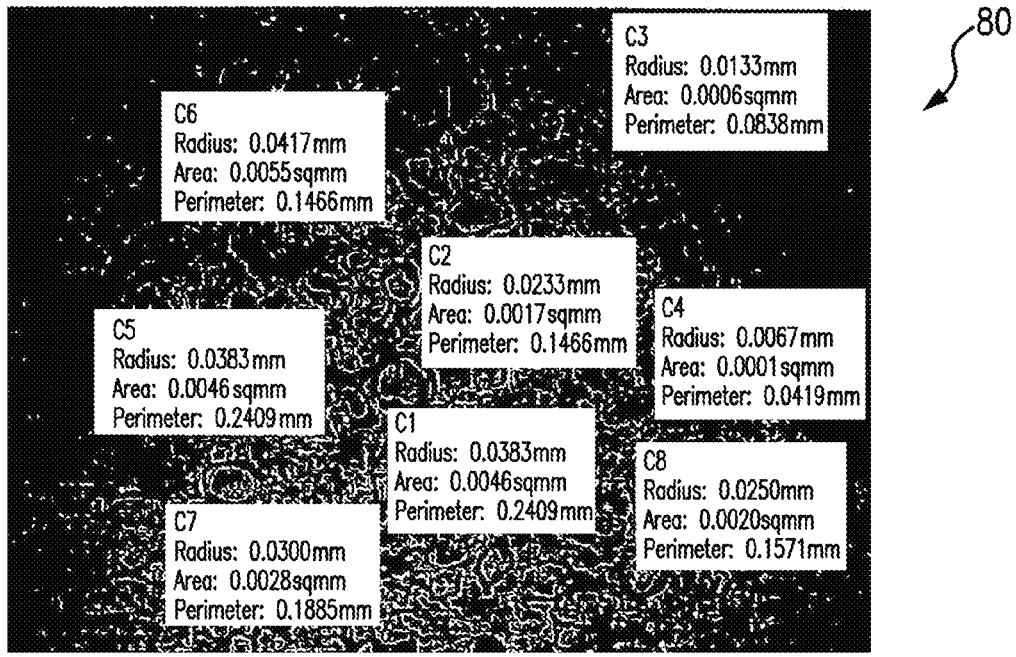
Figure 12:
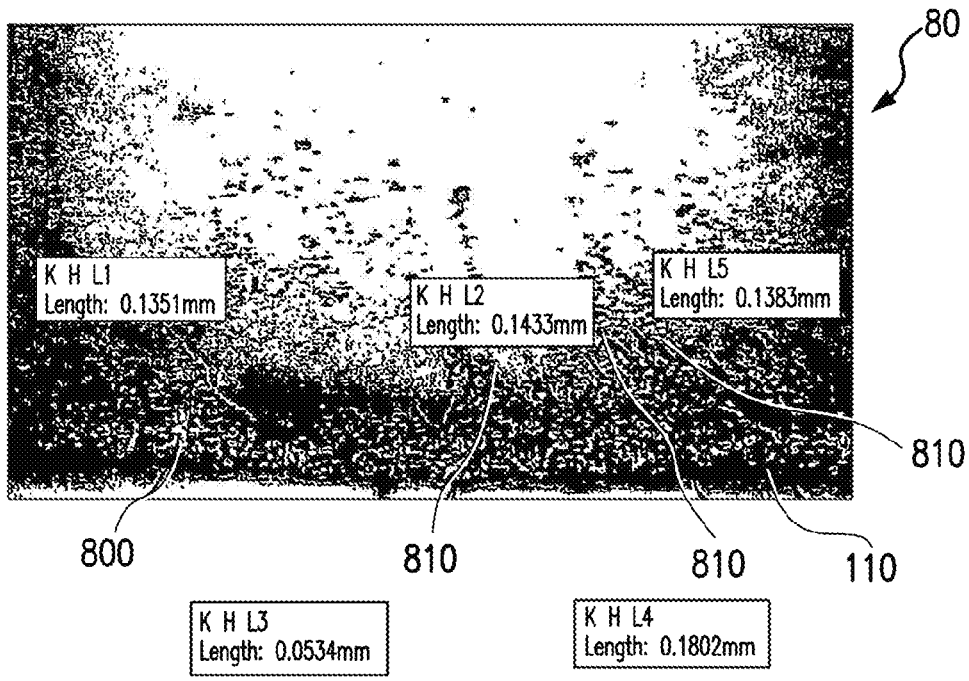
Figure 15:
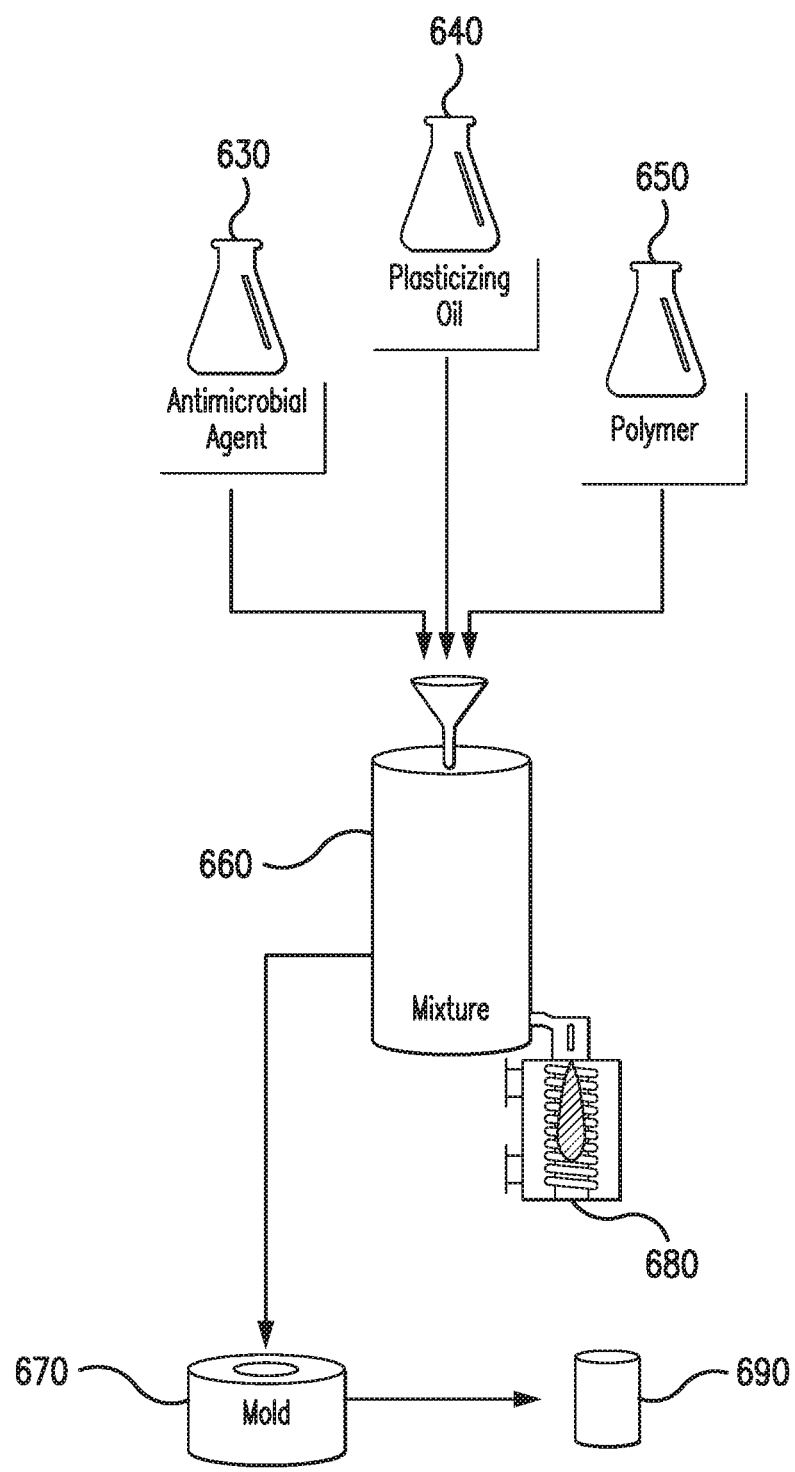
Figure 16:
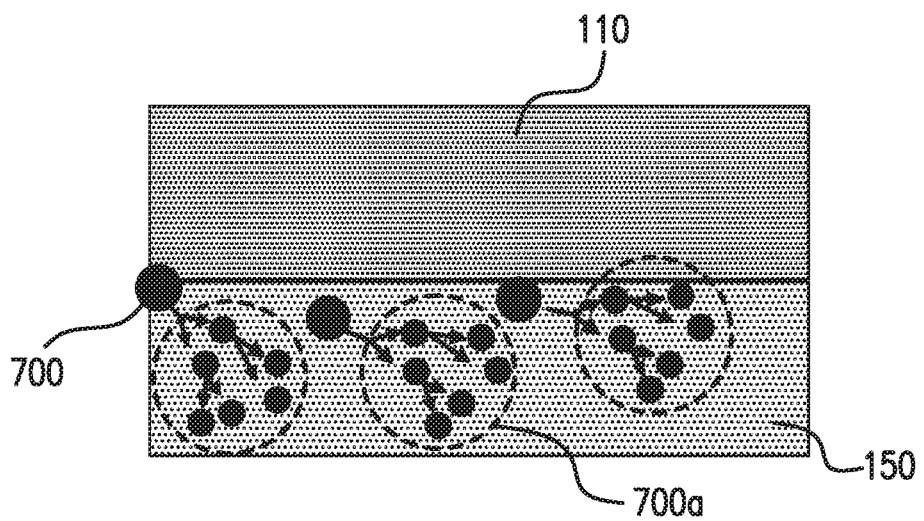
Figure 17:
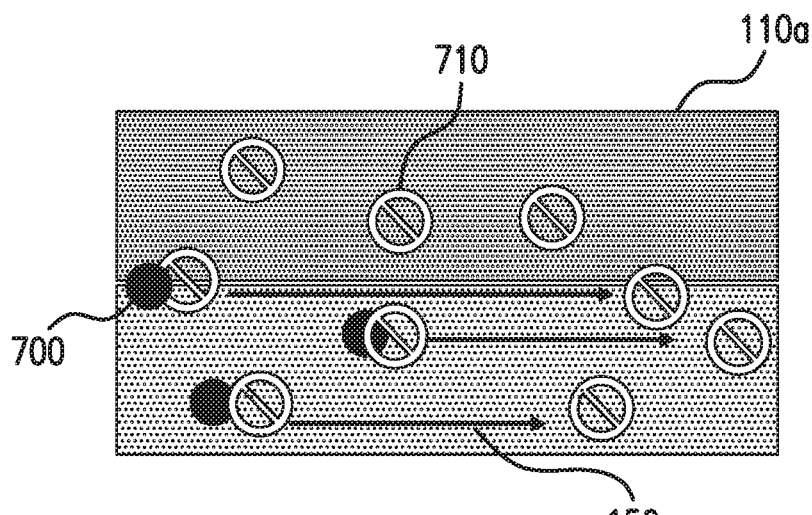
Figure 18:
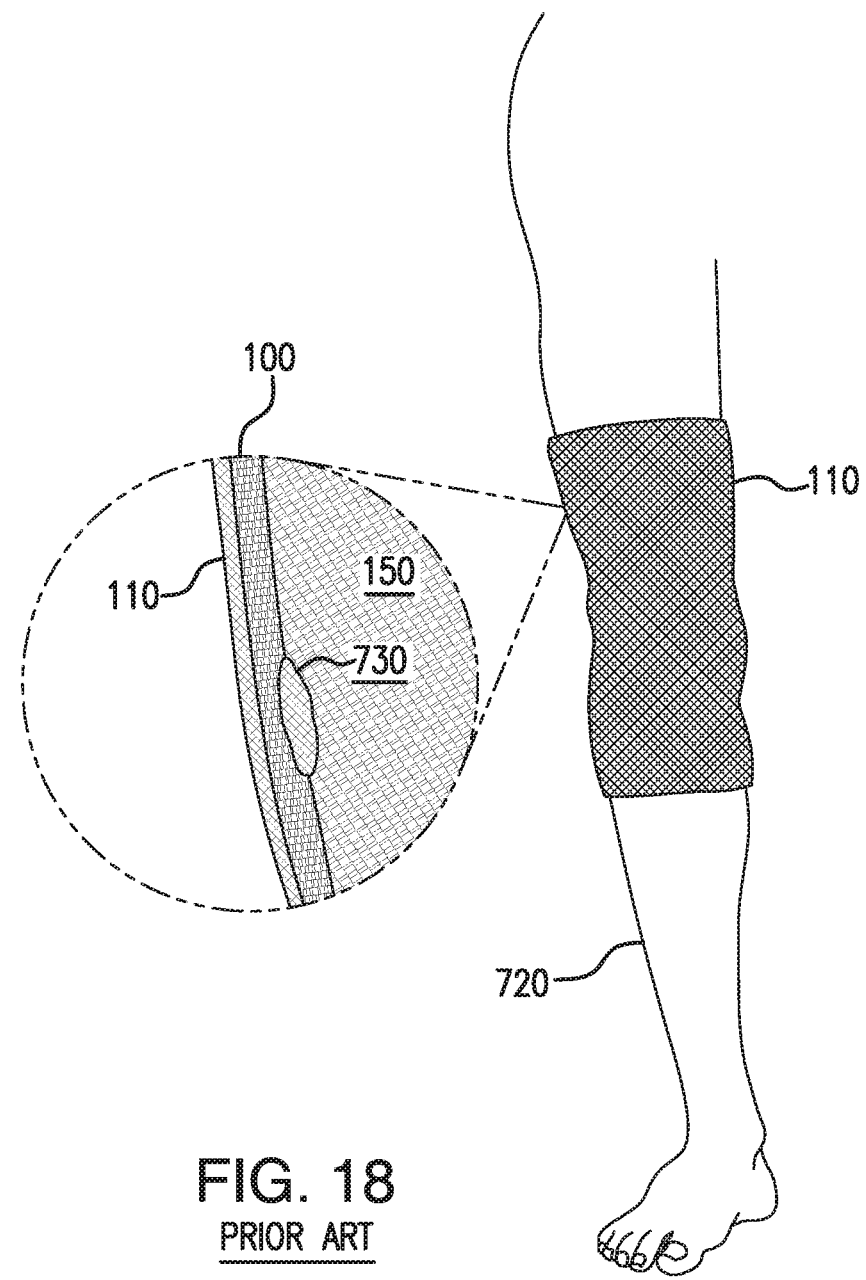
Figure 19:
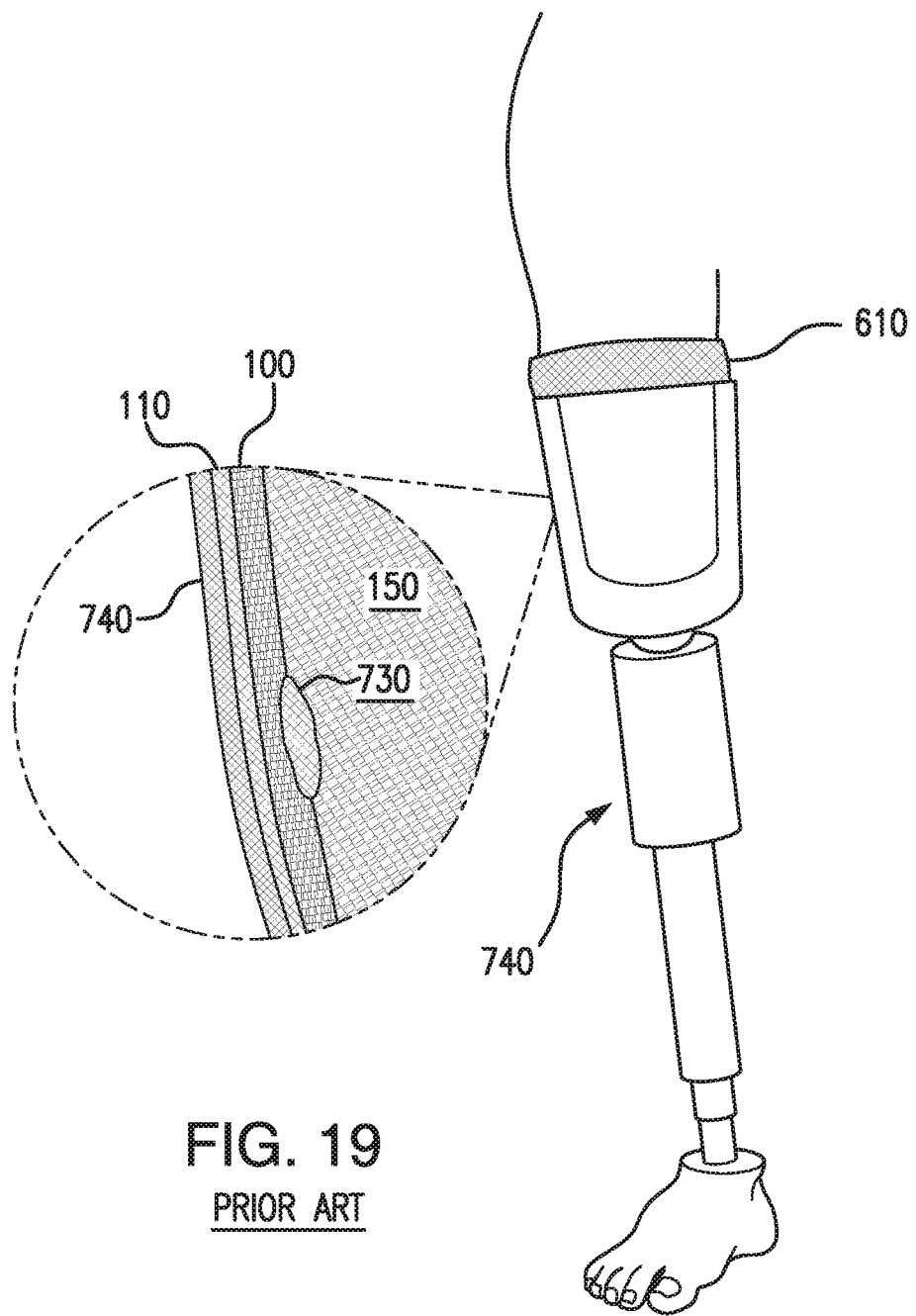
Figure 20A:
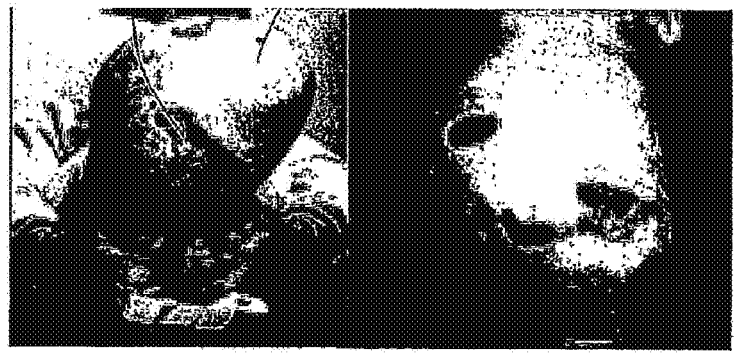
Figure 20B:
Figure 20C:
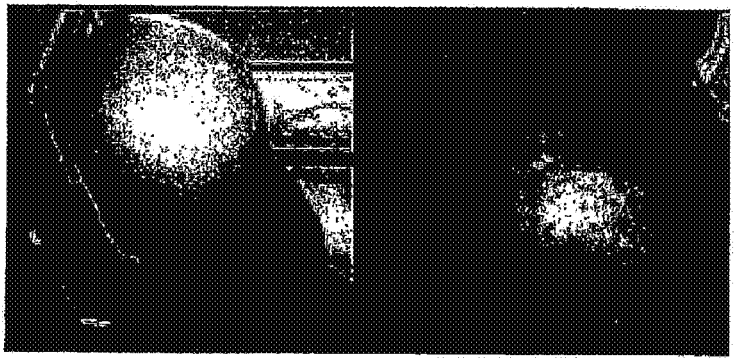

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4, and sub-ranges such as 1-3, from 2-4, and from 3-5, etc. as well as 1, 2, 3, 4, and 5 individually. The same principle applies to ranges recited only one numerical value as a minimum or a maximum. Furthermore, such an interpretation should apply regardless of the breadth of the range or the characteristics being described.

It is understood that any given particular aspect of the disclosed compositions and methods can be easily compared to the specific examples and embodiments disclosed herein. By performing such a comparison, the relative efficacy of each particular embodiment can be easily determined. Particularly preferred compositions and methods are disclosed in the Examples herein, and it is understood that these compositions and methods, while not necessarily limiting, can be performed with any of the compositions and methods disclosed herein.

Disclosed herein are garments having low thermal conductivity, high latent heat, high durability and resiliency. In certain aspects, the disclosed garments include compression garments configured to provide evenly distributed compressive forces (e.g., a high modulus of elasticity). When compared to currently used post-surgical garments, these garments (e.g., compression garments) advantageously result in better patient comfort and overall improved healing processes due to the combination of any of the following: (i) low thermal conductivity, (ii) high durability and resiliency, and in certain aspects (iii) evenly distributed compressive forces.

Each of the garments include a polymeric gel material, with the proviso that this gel material preferably is not a hydrogel. In other words, water content is highly limited within the gel (e.g., including water amounts of less than 1 wt %, 0.5 wt %, 0.3 wt %, or 0.1 wt % of the overall gel), or water, minus any impurities, may not be added to or within the disclosed polymeric gel. When compared with hydrogels, in certain aspects the disclosed gels preferably have lower thermal conductivity than hydrogels (and high heat capacity in certain aspects) so the disclosed gels draw less heat at a lower rate than hydrogels. These properties are preferable within the disclosed articles because the disclosed gels achieve better patient comfort and overall improved healing processes at an application site. In certain aspects, this gel material is made from a triblock copolymer and plasticizing oil and optionally includes one or more additives. However, to potentially reduce manufacturing costs and in certain preferred aspects, the gel material may only include the disclosed triblock copolymer(s), plasticizing oil, and optionally additives.

In certain aspects, triblock copolymer is a styrene-based polymer that includes styrene and at least one of ethylene, butadiene, butylene, propylene, or isoprene, for example a styrene-ethylene-ethylene-propylene-styrene, a styrene-ethylene-butylene-styrene, or a styrene-ethylene-propylene-styrene. In certain embodiments, thermoplastic elastomers according to the present invention comprises a polymer that is a hydrogenated poly(styrene-b-isoprene), a hydrogenated poly(styrene-b-isoprene-b-styrene), a hydrogenated poly(styrene-b-butadiene-b-styrene), a hydrogenated poly(styrene-b-isoprene/butadiene-b-styrene), or combinations thereof. In certain embodiments, the thermoplastic article comprises any of polystyrene-b-poly(ethylene/propylene) (SEP), polystyrene-b-poly(ethylene/propylene)-b-polystyrene (SEPS), polystyrene-b-poly(ethylene/butylene)-b-polystyrene (SEBS), or polystyrene-b-poly(ethylene-ethylene/propylene)-b-polystyrene (SEEPS), or any combination thereof. In certain aspects, the amount of triblock copolymer included within the gel material ranges from 50 to 500 parts per hundred, 75 to 300 parts per hundred, 90 to 200 parts per hundred, or 95 to 120 parts per hundred. In preferred aspects, the triblock copolymer is 100 parts per hundred and all other disclosed components (e.g., plasticizer/plasticizing oil, antioxidant, other additives) are weighed/weighted against the triblock copolymer. For example, if a 1:1.2 ratio of triblock copolymer to plasticizer is desired, this would be measured as 100 parts triblock copolymer and 120 parts plasticizer.

In certain aspects, the disclosed gels are made with and/or include one or more plasticizing oils that may include, for example, a paraffinic oil, naphtenic oil, a mineral oil, or a synthetic liquid oligomer of a polybutene, a polypropene, or a polyterpene oil. Suitable oils include plasticizing oils such as paraffinic oils, naphtenic petroleum oils, petroleum mineral oils, and synthetic liquid oligomers of polybutene, polypropylene, polyterpene, etc. may be used. In preferred aspects, the plasticizer is petroleum mineral oil with a viscosity of 10 to 20 centistokes, more preferably 11 to 17 centistokes, and most preferably 11 to 14 centistokes. In certain aspects, the plasticizing agent used within the gel includes petroleum mineral oil is 12 centistokes. The amount of plasticizer included within the gel ranges from 200 to 1000 parts per hundred, 250 to 750 parts per hundred, preferably 300 to 800 parts per hundred, more preferably 400 to 700 parts per hundred, and most preferably 500 to 650 parts per hundred. In certain aspects, the oil may also be seeded with an insoluble fine powder such as talc.

The oil or other plasticizing agent (also referred to herein as a plasticizer) can be added to the triblock copolymer in order to obtain the desired mechanical properties, such as elasticity, softness (or hardness), thermal conductivity, and elongation, tear and tensile strength characteristics of the resulting gel. For example, in some embodiments, suitable mechanical properties of the resulting gel include: (a) hardness between approximately 10 to 70 durometer on the Shore 00 scale, between 15 to 60 durometer on the Shore 00 scale, and more preferably about 15 to 40 durometer on the Shore 00 scale; (b) ultimate elongation of approximately 300 to 2000 percent, more preferably about 1500 percent; (c) tensile modulus at 300 percent elongation of between about 5 to 300 psi, more preferably about 30 psi; and/or (d) a thermal conductivity of 0.05 to 3.00 W/mk, 0.1 to 1.5 W/mk.

In certain embodiments, the disclosed gels may be manufactured by mixing together the styrene-based polymer, the plasticizing oil(s), and one or more optional additives, e.g., an antioxidant, an antimicrobial agent, and/or other additives, to form a mixture which is melted then cooled into the resulting gel. The additives may include, for example, 0.5 to 20 parts, 1 to 12 parts, or 1.5 to 8.5 parts. The antioxidants may include a phenolic antioxidant. For example, the phenolic antioxidant may include at least one of isobutylenated methylstyrenated phenol, a styrenated phenol, various o-, m-, p-cresols (e.g., 4,4'thiobis-6-(t-butyl-m-cresol), 4,4'-butylidenebis-b-(t-butyl-m-cresol)), 2,6-di-tert-butyl-p-cresol, (octadecanoxycarbonylether) phenol, tetrakis-(methylene-(3,5-ditertbuty-4-hydrocinnamate)methane, 2,2'-methylenebis(4-methyl-6-nonyl) phenol, 1,3,5-tris(3,5-di-tert-butyl-4-hydroxybenxyl+1,3,5-triazine-2,4,6 (1H,3H, 5H)-trione, or any combination thereof, which may each independently range from 1 to 8 parts per hundred or 2 to 5 parts per hundred or in combination may range from 1 to 8 parts per hundred or 2 to 5 parts per hundred. The antimicrobial agents may include, for example, at least one of silver zeolite, silver zirconium phosphate, silver nitrate, silver thiosulfate, silver sulphadiazine, silver fusidate, and quaternary ammonium compounds (QAC). Other classes of silver-based antimicrobial agents may be used as well, for example a silver acetate, a silver bromide, a silver carbonate, a silver chlorate, a silver chloride, a silver citrate, a silver fluoride, a silver iodate, a silver lactate, a silver nitrate, a silver nitrite, a silver perchlorate or a silver sulfide. In addition, one or more other antimicrobial agents may be used in conjunction with or instead of such silver-based antimicrobial agents. When present, the antimicrobial agent, may only include from 0.3 to 1 wt % or from 0.5 to 0.9 wt % of the overall weight of the gel. In certain aspects, the antimicrobial agent may range from 50 to 200 parts per hundred, preferably 65 to 175 parts per hundred, and most preferably 80 to 150 parts per hundred. These antioxidants and antimicrobial agents may be included within the gel to further enhance the therapeutic purposes of the resulting gel and embodiments disclosed herein. For example, in certain aspects, the antioxidants and/or antimicrobial agents may seep out from the gel onto the wearer's skin and/or bandages. In theory, the antioxidants and/or antimicrobial agents that seep from the gel may contact the surgical site or areas around the surgical site, thus resulting in beneficial delivery of these antioxidants and/or antimicrobial agents that further aid in improved and expedited healing of the surgical site(s).

In alternative aspects, one or more of the above discussed additives may be added to the mixture after the mixture is melted or during the cooling process. After heating and mixing the mixture of styrene-based polymer, the plasticizing oil(s), and one or more optional additives, these components are melted together in such a manner that a homogeneous, molten mixture is obtained. After obtaining the molten mixture, the molten mixture is extruded via an extruder, molded via a molding machine, or other similar heated vessel into the desired shapes and thickness. In certain aspects and when the disclosed gels are included in the disclosed garments and have a thickness ranging from 0.050 inches to 0.625 inches, more preferably 0.0625 inches to 0.400 inches in thickness, and most preferably 0.1 inches to 0.3 inches. These thicknesses are desired to ensure that maximum reduction and/or prevention of post-surgical, excessive bruising, swelling, and edema associated with surgical procedures.

The present invention provides thermal therapy to localized site and does so more effectively due to the heat available during the latent heat of fusion. The thermoplastic elastomer utilizes a plasticizing oil that is able propagate the active ingredients, that are soluble in the oil phase, through the dermis of a localized area. When the material is heated to the phase change temperature and placed on a localized site, the formability of the material, in conjunction with the heat, allows for a greater efficacy of the active ingredients therein.

Table II includes examples of suitable active ingredients but broadly include nonpolar substances used in treatment of disease.

TABLE 1

| Antioxidant Additives | Chemical Name |
| --- | --- |
| 1 | Acyclovir |
| 2 | Zidovudine, also known as azidothymidine (AZT) |
| 3 | Azithromycin |
| 4 | Benzoyl peroxide |
| 5 | Ceftriaxone |
| 6 | Clindamycin |
| 7 | Clotrimazole |
| 8 | Doxycycline |
| 9 | Erythromycin |
| 10 | Metronidazole |
| 11 | Nystatin |
| 12 | Povidone iodine |
| 13 | Sulfasalazine |
| 14 | Tolnaftate |

Figure 21:
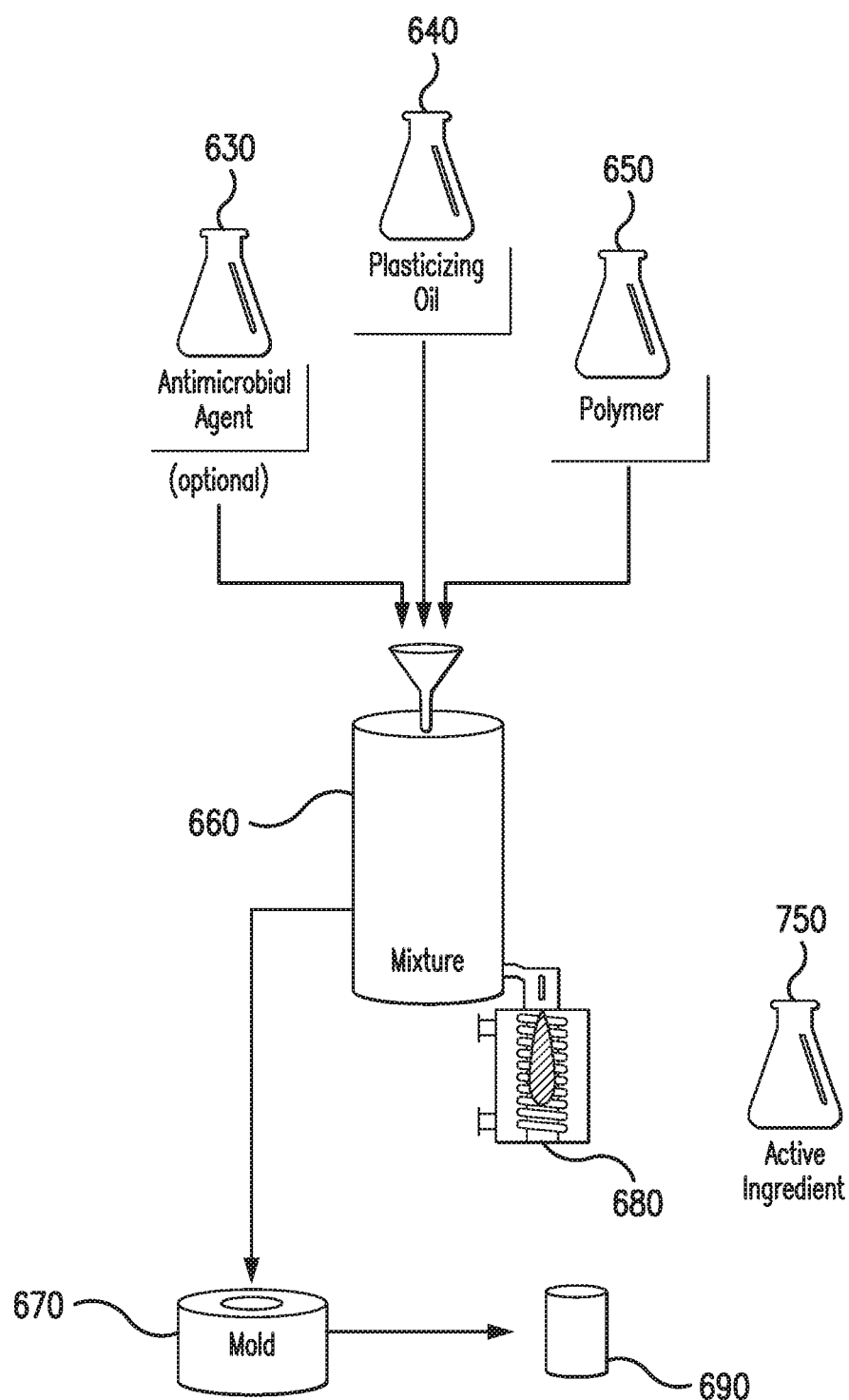
FIG. 21 is a diagrammatic view of an embodiment of the invention.
Figure 22:
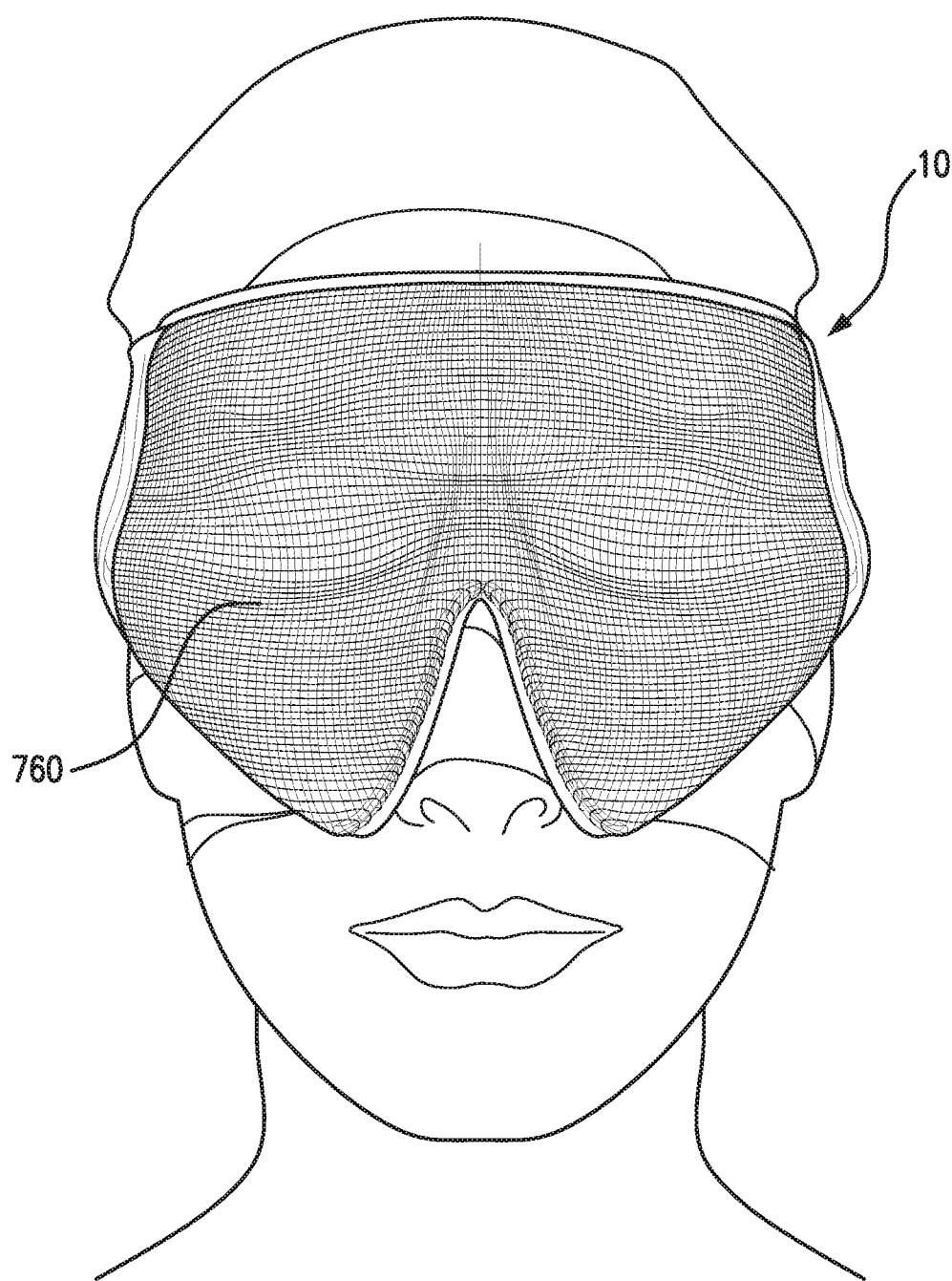
FIG. 22 is a front view of the treatment garment according to the first embodiment being worn by a wearer.

Referring to FIG. 21, a process of making an elastomer incorporating active ingredients used for the treatment of diseases includes combining an antimicrobial agent 630, plasticizing oil 640, and polymer 650 to form mixture 660. Polymer 650 is preferably a styrene block copolymer. Heat 680 is applied to mixture 660. Plasticizing oil 640 may be heated prior to or after the addition of the antimicrobial agent 630 and polymer 650. Mixture 660 is melted in an extruder, a molding machine, or other suitable heated vessel so that the antimicrobial agent 630 becomes suspended in the mixture 660 and remains in stable suspension with the mixture 660. The molten mixture 660 is molded 670 into the form of a useful item at an appropriate temperature. While the mixture 660 cooling, and when the temperature is below 100° F. or 37° C., the active ingredient 750 is added to the mixture 660. When allowed to cool, e.g., towards room temperature of approximately 77° F. or 25° C., the mixture 660 solidifies and forms elastomer 690.

If the plasticizing oil 640 is heated before mixing, an appropriate temperature range is about 130° to 165° F. Plasticizing oils such as paraffinic oils, napthenic petroleum oils, mineral oils, and synthetic liquid oligomers of polybutene, polypropylene, polyterpene, and the like may be used. In some embodiments, 300 to 1,200 PPH of the plasticizing oil are used, more preferably between about 500 and 700 PPH.

Preferably, the compound contains 50 to 90 percent by weight of plasticizing oil, 0.5 to 30 percent by weight of active ingredient, and 3 to 50 percent by weight of a paraffinic substance. Paraffinic substances are used in order to take advantage of the latent heat used to cause the phase change.

Figure 23:
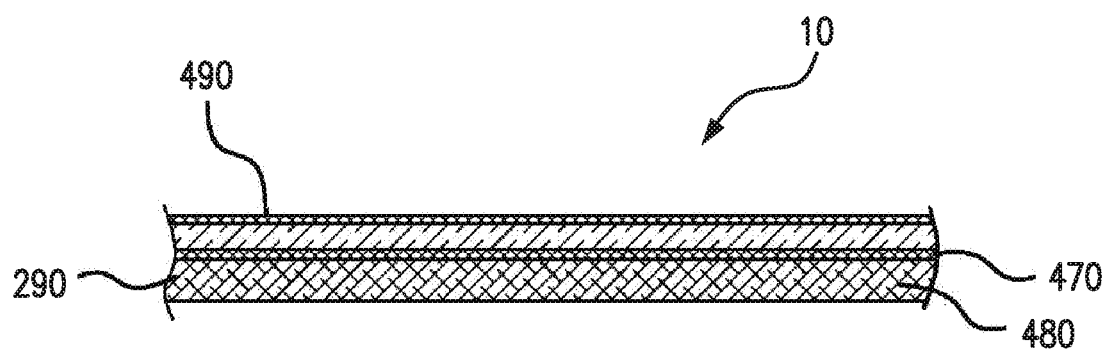
FIG. 23 is a cross-section of the layers included within the treatment garment according to the first embodiment.
Figure 24:
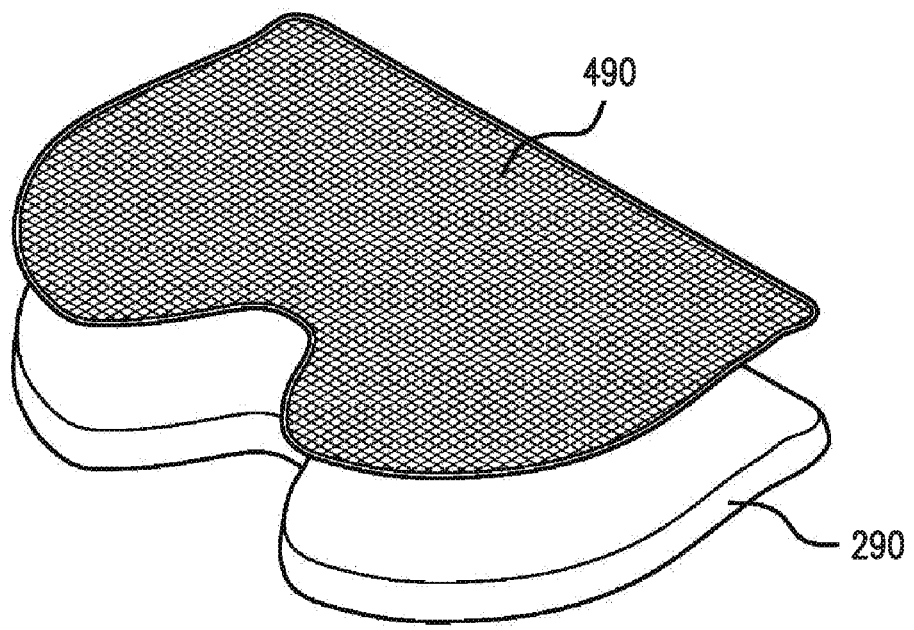
FIG. 24 is an exploded view of the layers included within the treatment garment according to the first embodiment.
Figure 25:
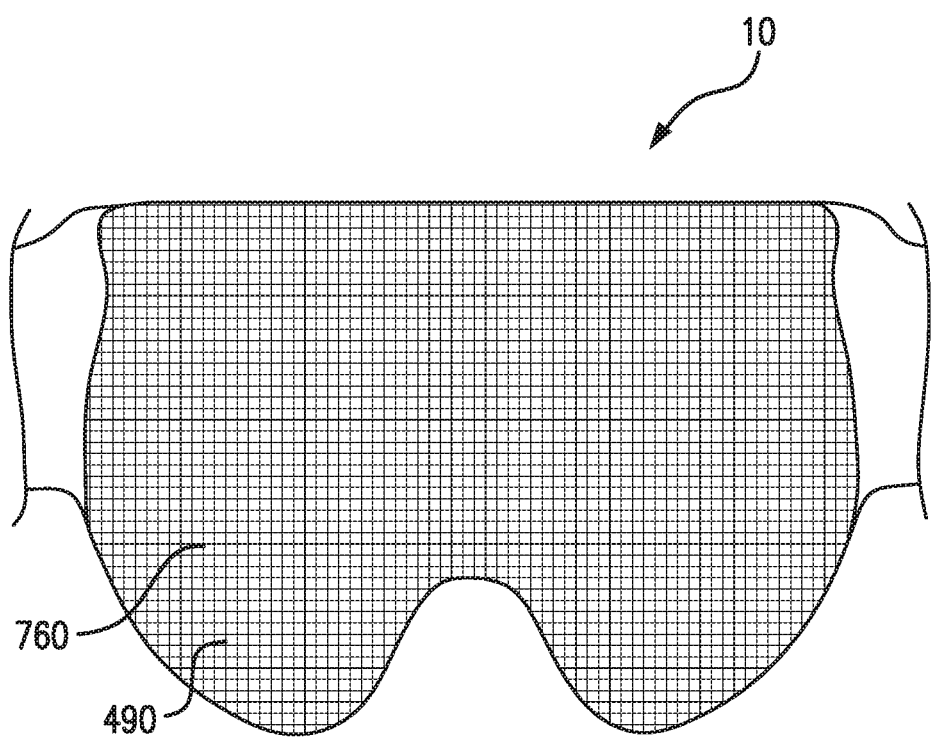
FIG. 25 is a back view of the treatment garment according to the first embodiment.
Figure 26:
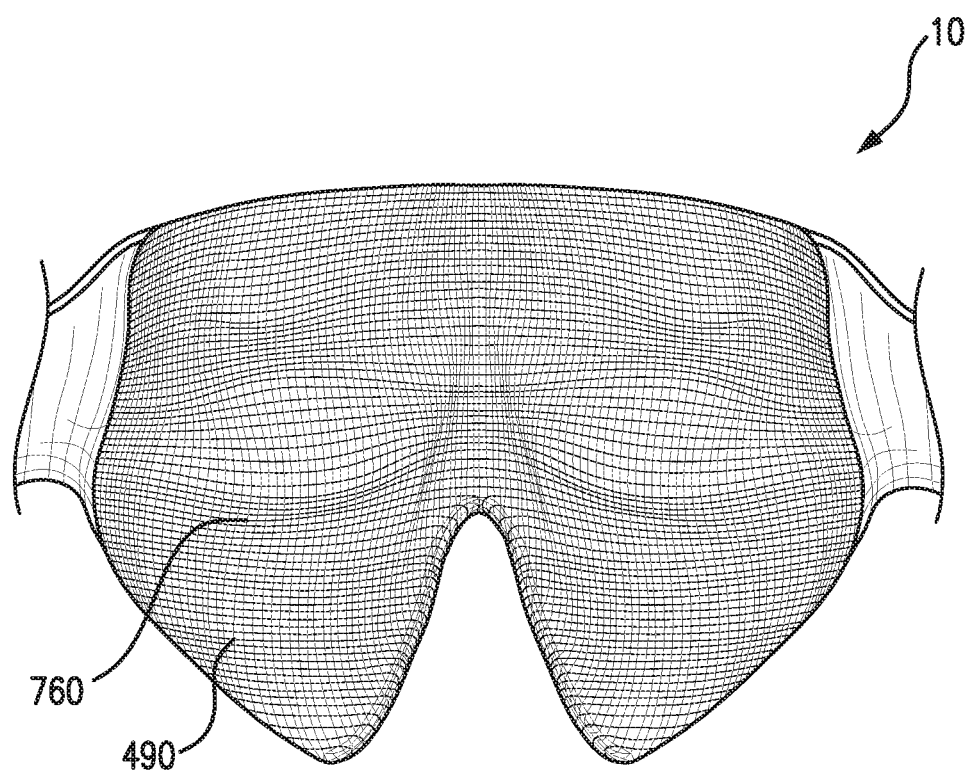
FIG. 26 is a front view of the treatment garment according to the first embodiment.
Figure 27:
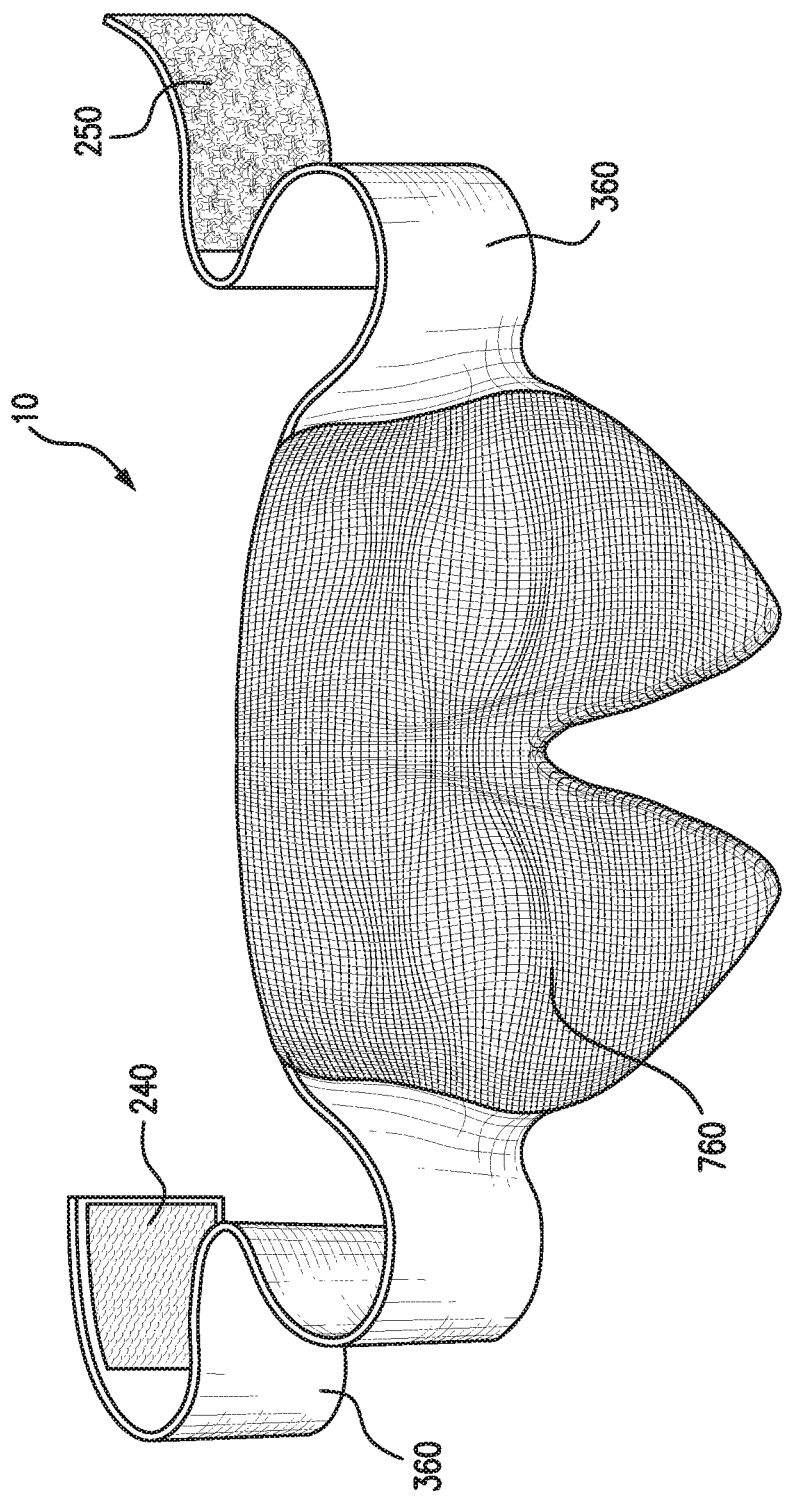
FIG. 27 is a front view of the treatment garment according to the first embodiment including straps and hook and loop fasteners.
Figure 28:
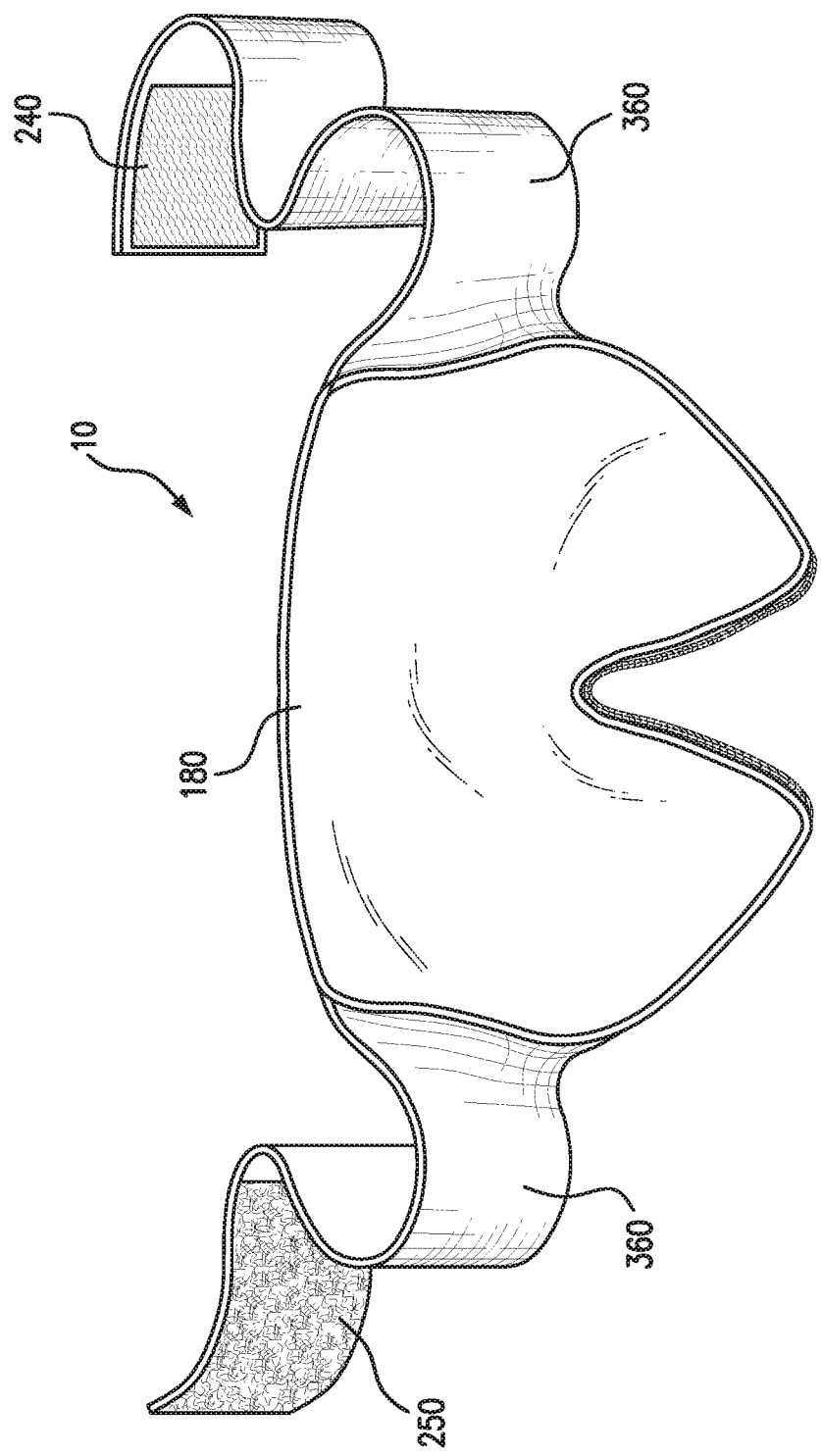
FIG. 28 is a back view of the treatment garment according to the first embodiment including straps and hooks and loop fasteners.

The disclosed garments will now be described in more detail with reference to the Figures. FIGS. 22-28 disclose a treatment garment 10 according to a first embodiment including a thermoformable composite 760 comprising an outer layer 490 and gel layer 290, the thermoformable assembly 760 configured to be heated to a glass transition temperature of the thermoformable paraffinic gel that comprises the gel layer 290 such that the thermoformable assembly can be shaped to conform to contours of a user's face. In this aspect, the treatment garment 10 includes a styrene-based polymeric gel layer 290 arranged on the outer layer 490 As depicted in FIG. 23, when in use, gel layer 290 of treatment garment 10 is placed on bandage 470, which directly covers flesh and/or post-surgical site 480. However, in certain aspects, the gel layer 290 is configured to directly contact the wearer's skin/flesh.

In certain aspects, a thermoformable resin may be included and comprises at least one of a co-polyester, a poly-caprolactone, nylon, polypropylene, polyethylene, or a combination thereof. In certain aspects, the thermoformable resin is a low melt resin configured to begin melting or completely melt at temperatures ranging from 100° degree F. to 300° degree F., 120° degree F. to 250° degree F., 120° degree F. to 200° degree F., 120° degree F. to 150° degree F., 130° degree F. to 175° degree F., 130° degree F. to 150° degree F., 135° degree F. to 145° degree F., 140° degree F. to 160° degree F. In certain aspects, the thermoformable assembly is configured to be heated to a temperature of no more than 5° degree F., 10° degree F., 20° degree F., 35° degree F., 50° degree F., 65° degree F., 80° degree F., 100° degree F., or 120° degree F. above the glass transition temperature of the thermoformable resin. The thermoformable resin may initially include a body made from a low-melt co-polyester yarn (e.g., having a melting temperature of under 200° degree F.), a poly-caprolactone yarn, nylon yarn, polypropylene yarn, polyethylene yarn, or a combination thereof. In certain aspects, the thermoformable resin and/or the body that becomes the thermoformable resin may include any combination of a low-melt co-polyester yarn, a poly-caprolactone yarn, nylon yarn, polypropylene yarn, and polyethylene yarn and a polyester fiber (having a melting temperature above 300° degree F. and ranging from 300° degree F. to 500° degree F., preferably 300° degree F. to 400° degree F.). These low-melt yarns may preferably have a mass ranging from 110 to 160 denier, 120 to 150 denier, 130 to 145 denier, and 135 to 145 denier. This body is preferably made on traditional machinery.

In certain aspects, the outer layer 490 are selected to further synergistically maximize the reduction and/or prevention of post-surgical, excessive bruising, swelling, and edema associated with surgical procedures. For example, these fabric layers and the yarns included in the fabric layers and the filaments included within the yarns of the layers may be selected to maximize compressibility of the gel to further maximize post-surgical treatment for the reduction and/or prevention of bruising, swelling, and edema. Depending on the desired effects, the inner and outer fabric layer are the same, or alternatively, the inner and outer fabric layer are different. For example, the inner and outer layer fabric layers may independently be made from, for example, a non-low melt polyester yarn, a non-low nylon yarn, a non-low polypropylene yarn, a non-low melt polyethylene yarn, cotton yarn, wool yarn, any combinations thereof, and these yarns may be either multifilament or monofilament. In certain aspects, the yarns included within the inner and outer layer fabric layers are multifilament having a mass ranging from 110 to 160 denier, 120 to 150 denier, 130 to 145 denier, and 135 to 145 denier. In certain aspects, the fabric of the inner and outer fabric layers have multidirectional stretch characteristics that aid in further enhancing durability of the thermoformable assembly. The fabric of the inner and outer fabric layers may independently include from 6 to 12 courses per $cm^2$, more preferably from 8 to 10 courses per $cm^2$ and from 9 to 14 wales per $cm^2$ more preferably 10 to 12 wales per $cm^2$. In certain preferred aspects, the inner and outer fabric layers independently include 9 courses and 11 wales per $cm^2$. In certain aspects, the fabric of the inner and outer fabric layers independently have an elasticity ranging from 80 to 140%, preferably 100 to 130%, and most preferably 115 to 125% in a vertical direction and from 60 to 100%, preferably 70 to 90%, and most preferably 75 to 85% in the horizontal direction.

When initially making the thermoformable assembly, the body made from a co-polyester yarn, a poly-caprolactone yarn, or a combination thereof and optionally having a polyester fiber may be positioned in between the inner and outer layer fabric layers. After layering this stack, this layered stack is heated to a sufficient temperature to melt the body from a co-polyester yarn, a poly-caprolactone yarn, or a combination thereof to bond these layers together. In certain aspects and because the body from a co-polyester yarn, a poly-caprolactone yarn, or a combination thereof includes fabric "windows", this body of co-polyester yarn, a poly-caprolactone yarn, or a combination thereof may be preferred over a solid sheet (e.g., a laminate layer) made from the same material because the windows and structure may allow for stronger bonding while concurrently lowering manufacturing costs of the thermoformable assembly. However, in certain alternative aspects, a solid sheet of the thermoformable resin may be used when manufacturing the thermoformable assembly. In additional aspects, the thermoformable assembly is preferably configured to be repeatedly heated and reshaped to the user's contours. For example, with regard to a rhinoplasty, the thermoformable assembly may be heated to or slightly above the thermoformable resin's glass transition temperature to ensure that the thermoformable assembly may be shaped to the user's contours. It is important that thermoformable resin hardens and becomes rigid after heating to (or beyond) its glass transition temperature. However, it is also important that the thermoformable resin does not become brittle after heating such that the thermoformable assembly is fragile, lacks durability, and may not be re-heated and/or re-shaped. Thus, the disclosed thermoformable assembly may be advantageously repeatedly heated and re-shaped into a rigid structure having desired contours.

The styrene-based gel is used in combination with the thermoformable assembly, and in certain aspects, the styrene-based gel is removable from the thermoformable assembly. However, in other aspects, the styrene-based gel is permanently attached to the thermoformable assembly. In each of these aspects, the styrene-based gel has a thickness ranging from 0.05 inches to 0.625 inches, more preferably 0.1 inches to 0.5 inches, and most preferably 0.250 to 0.50 inches to further ensure maximum reduction and/or prevention in post-surgical bruising, swelling, and edema.

The mask further includes a strap 360 configured to secure around a user's head to hold the mask in place on the user's face, and the mask includes hook and loop fasteners 370, 380 for securing the strap to the mask. In certain aspects, the hook or loop fastener may be attached to one end of the strap and the complimentary hook or loop fastener may be attached on the thermoformable assembly 760 or on another strap. For example, in certain aspects, the mask includes two straps 370, 380 configured to secure around a user's head to hold the mask in place on the user's face.

The treatment garment 10 may preferably be a partial face mask configured for placement over a user's eyes and the bridge of the nose. The styrene based gel of this partial face mask can be heated and/or cooled to a desired temperature and applied and fastened to the user's face to treat post-surgical bruising, swelling, and edema associated with, for example, rhinoplasty, eyelid surgery, check implantation, or any combination thereof. This treatment garment 10 is preferred over conventional hydrogel masks because unlike hydrogel based masks, this mask exhibits low thermal conductivity and high durability and resiliency coupled with the ability to provide evenly distributed compressive forces (e.g., a high modulus of elasticity). Additionally, this mask 10 advantageously results in better patient comfort and overall improved healing due to the combination of any of (i) low thermal conductivity, (ii) high durability and resiliency, (iii) evenly distributed compressive forces, and (iv) customizability or formability achieved by treatment garment 10. In certain aspects, post-surgical mask 10 further includes, for example, fabric or a fabric layer that lines the peripheral edges of mask 10 and conceals one or more layers of the thermoformable assembly. For example, in certain aspects, the fabric or fabric layer completely lines the peripheral edges of mask 10 and completely conceals the thermoformable assembly such that the thermoformable assembly is not visible to the wearer or another observer. In certain aspects, mask 10 is more aesthetically pleasing when the fabric or fabric layer lines the peripheral edges of mask 10.

Figure 29:
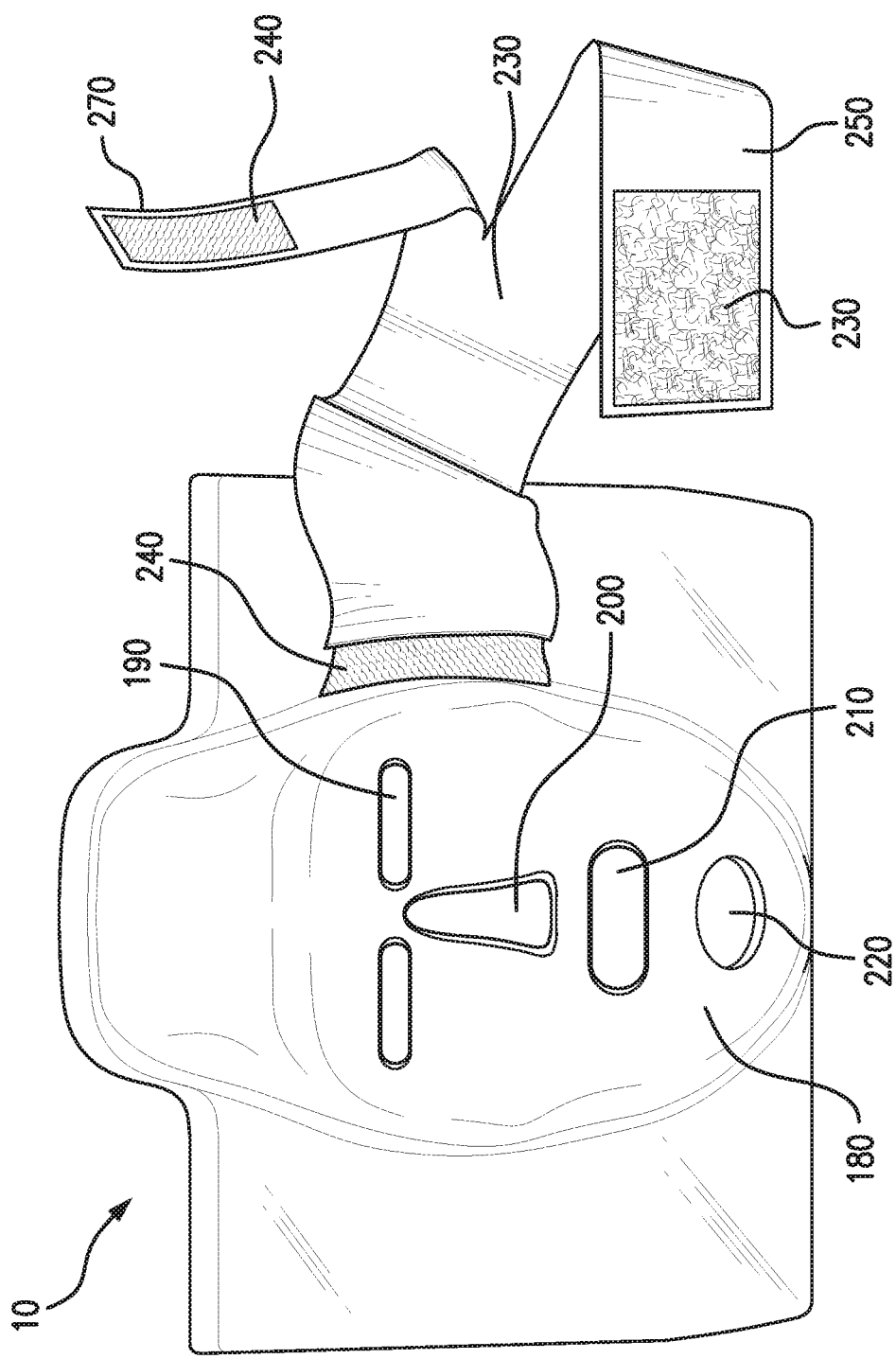
FIG. 29 is a front view of the mask according to a second embodiment of the invention.
Figure 30B:
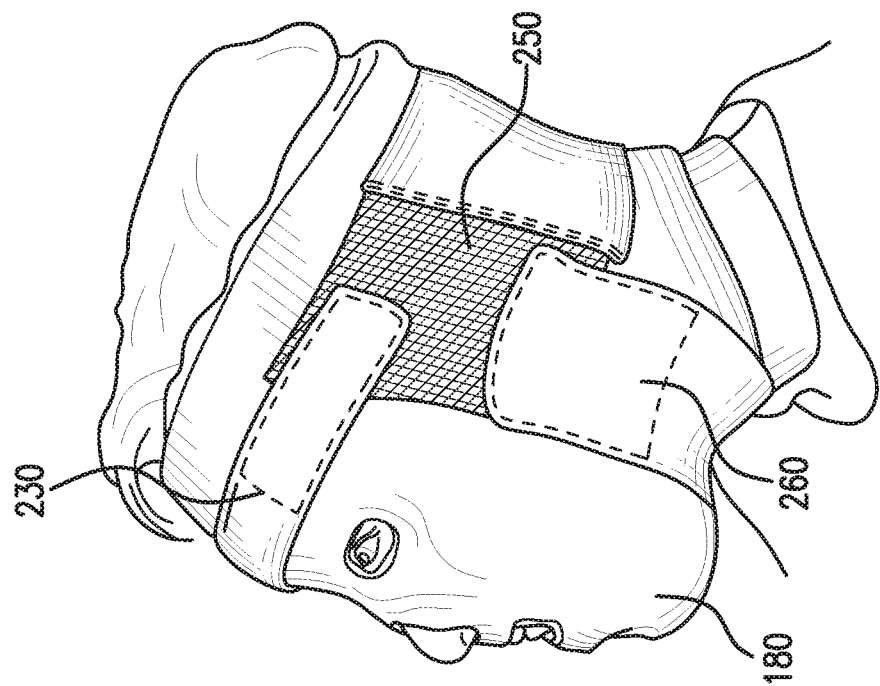
FIGS. 30(a) and 30(b) shows multiple side views of the mask according to a second embodiment of the invention.
Figure 30A:
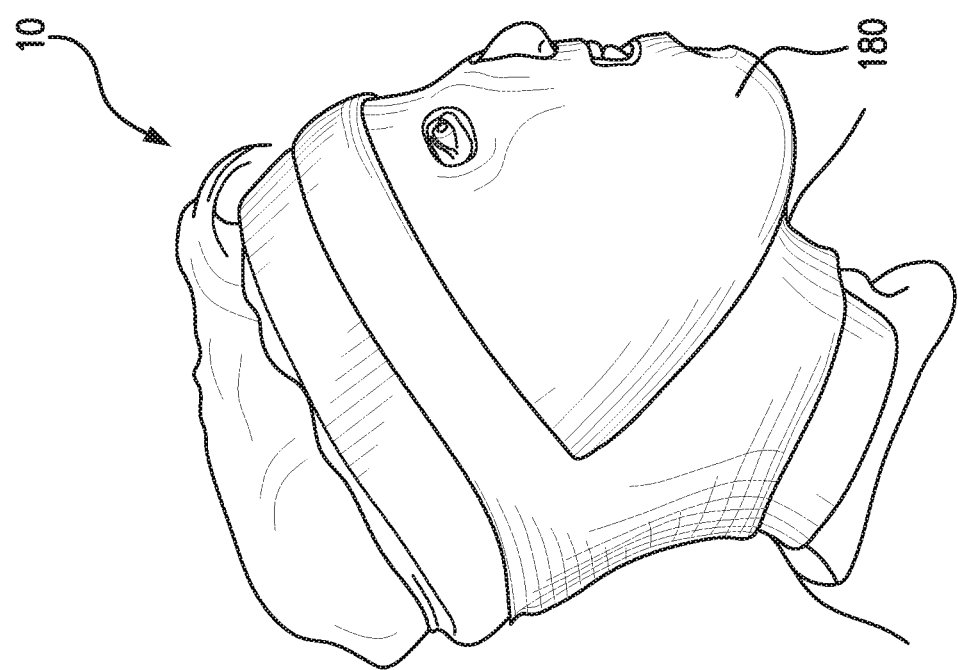

In another embodiment and as further illustrated in FIGS. 29, 30(a), and 30(b), the garment may include a treatment garment 10 including a mask 180 made from a styrene-based gel shaped to conform to and cover a wearer's face including a chin, a nose, cheeks, forehead, and ears, the mask having openings at the wearer's eyes 190, nose 200, mouth 220, and optionally the chin 230; and a mask strap 360 configured to fasten around the forehead and under the chin to secure the mask in place. For example, this treatment garment 10 may consist essentially of or consist only of the styrene-based gel, which conforms to and covers a wearer's face including a chin, a nose, cheeks, forehead, and ears, the mask having openings at the wearer's eyes, nose, and mouth, and a strap configured to fasten around the forehead and under the chin to secure the mask in place. In certain aspects, the strap includes complimentary hook and look fasteners 370, 380 on opposite ends of the strap. One end of the strap may be bifurcated such that a portion of the bifurcated strap 260 wraps around the chin of a user while a second portion of the bifurcated strap 270 is configured to wrap around the head of the user in such a manner that the mask may be securely fastened to a user with the strap. In certain aspects, the strap is an elastic strap configured to stretch and apply compressive forces when securely fastening the mask to the user. As illustrated in FIGS. 29, 30(a), and 30(b) the mask strap 360 may be attached to, for example, on the outermost surface of the gel, or in certain aspects, the mask strap 360 may be positioned within the gel.

Figure 35:
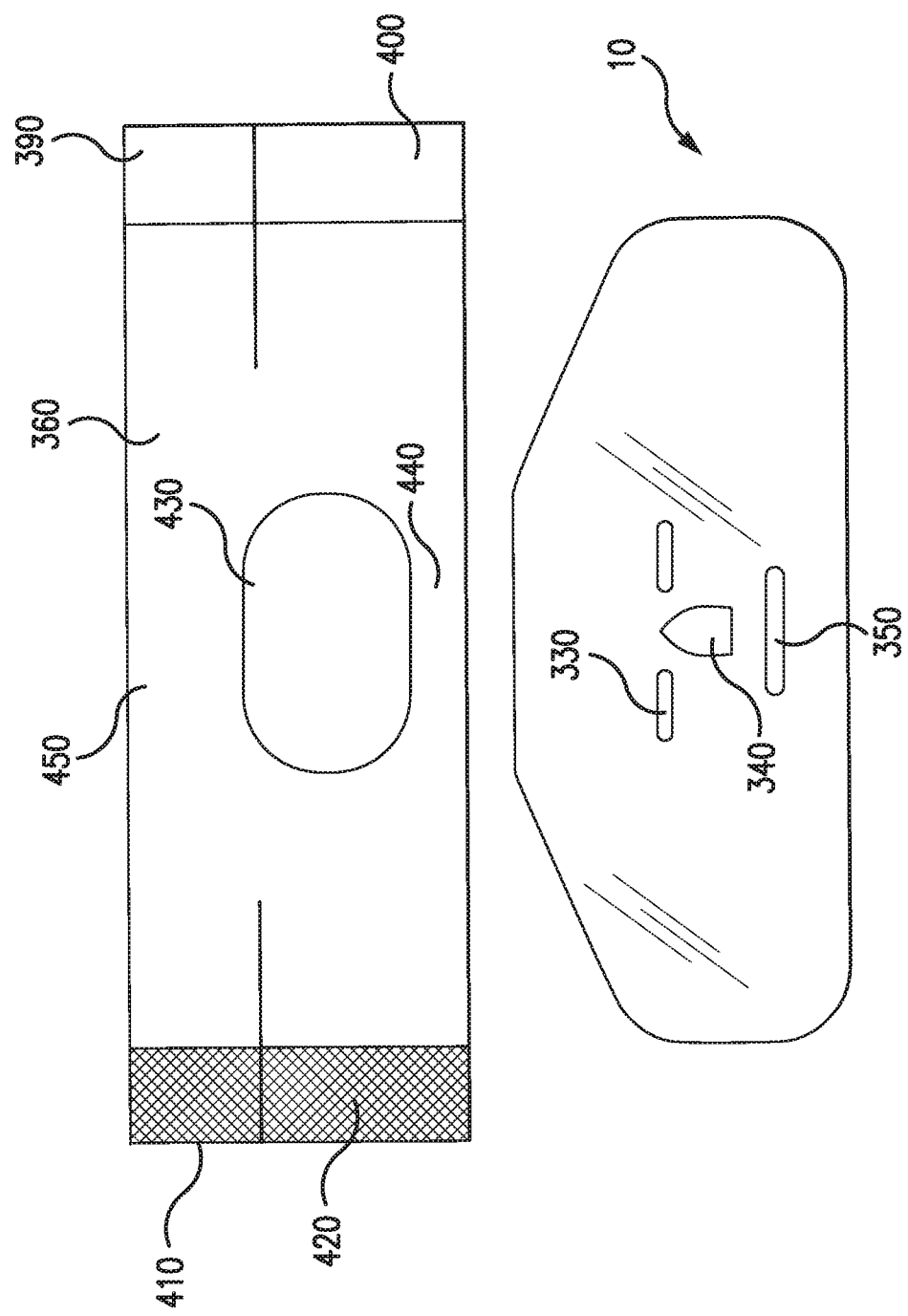
FIG. 35 is a top view of another embodiment of the treatment garment.
Figure 36:
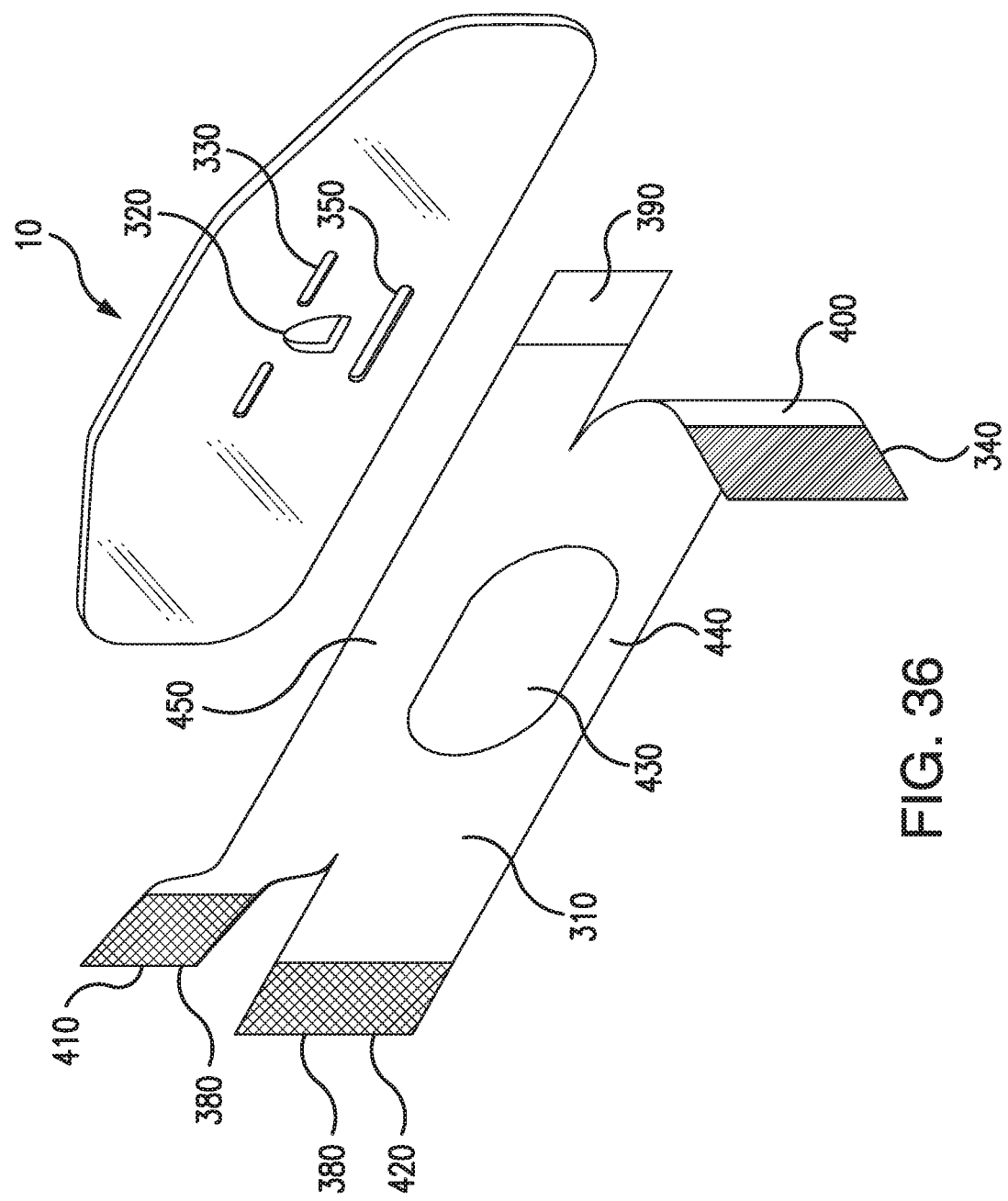
FIG. 36 is a perspective view of the treatment garment of FIG. 35.

As further illustrated in FIGS. 35 and 36, in certain aspects, the mask strap 360 may have various alternative shapes and configurations. For example, the mask strap 360 may be bifurcated at both ends 390, 400, 410, 420. These bifurcated ends 390, 400, 410, 420 may further include complementary hook 370 and loop 380 fasteners. As further illustrated in FIGS. 35 and 36, the mask strap 360 may include a hole 430 positioned mid-span along the length of the mask strap 360 such that portions 440, 450 of the strap are configured to concurrently wrap around a wearer's chin and forehead respectively while not contacting and/or obstructing any of the wearer's nose, eyes, mouth, and combinations thereof. The mask depicted in FIGS. 35 and 36 may also include a styrene based gel mask 190 that is removable or permanently attached to mask strap 360. In certain aspects, the styrene based gel mask 190 and the mask strap 360 are two separate components that are not permanently attached to one another. In this aspect, the styrene based gel mask 190 may further include eyeholes 330, a nosehole 340, and mouth hole 350 such that the mask 190 can be placed on, for example, the wearer's face, and then the mask strap 360 including the hole can be positioned over the styrene based gel mask to secure the mask to the wearer. For example, the mask strap 360 may be placed on the wearer such that portions 440, 450 of the strap around the hole 430 secure the forehead and chin portions respectively of the styrene based gel to the wearer and then the strap may be fastened by the hook and loop fasteners positioned on the bifurcated ends 390, 400, 410, 420. The mask 190 can have any number of openings to receive facial orifices.

Figure 37A:
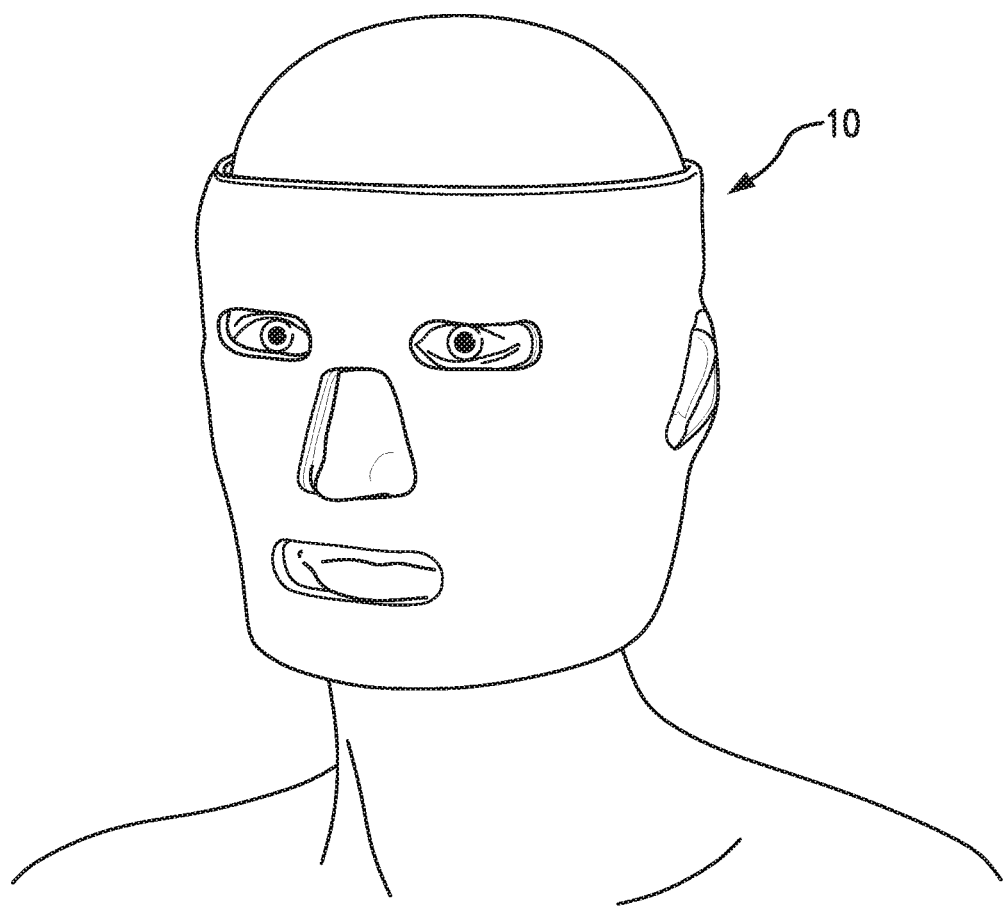
FIGS. 37(a) and 37(b) show another embodiment of the post-surgical mask having a thermoformable assembly and the styrene based gel.
Figure 37B:
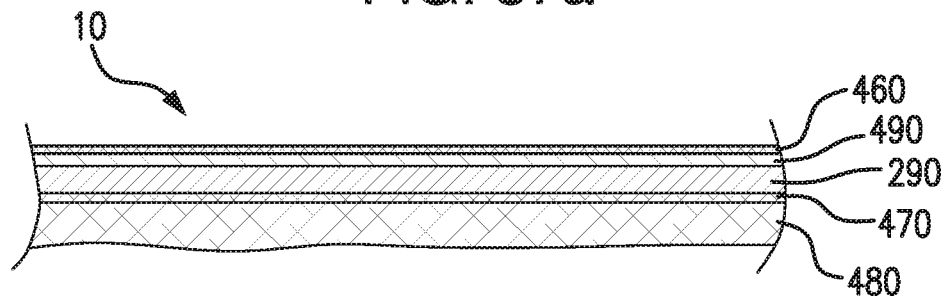
Figure 38A:
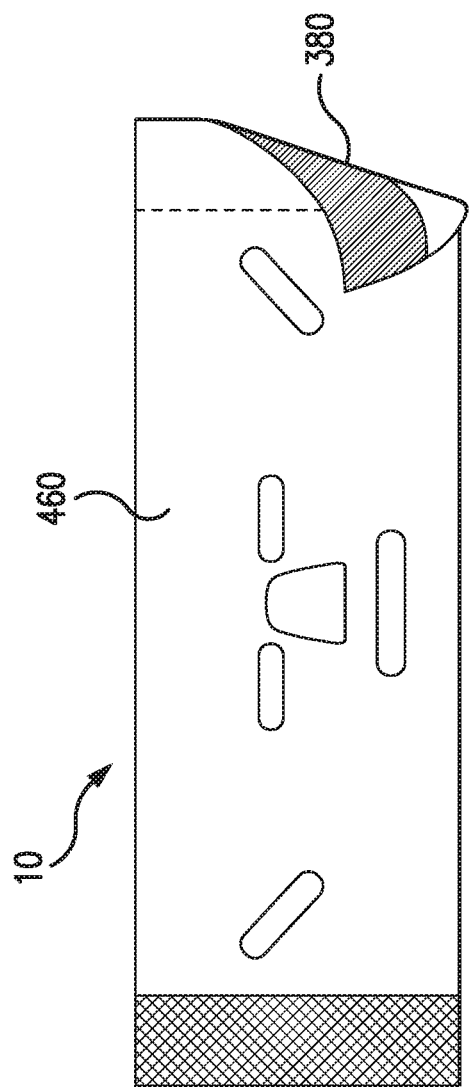
FIGS. 38(a) and 38(b) show the various perspective view of the treatment garment of FIG. 35.
Figure 38B:
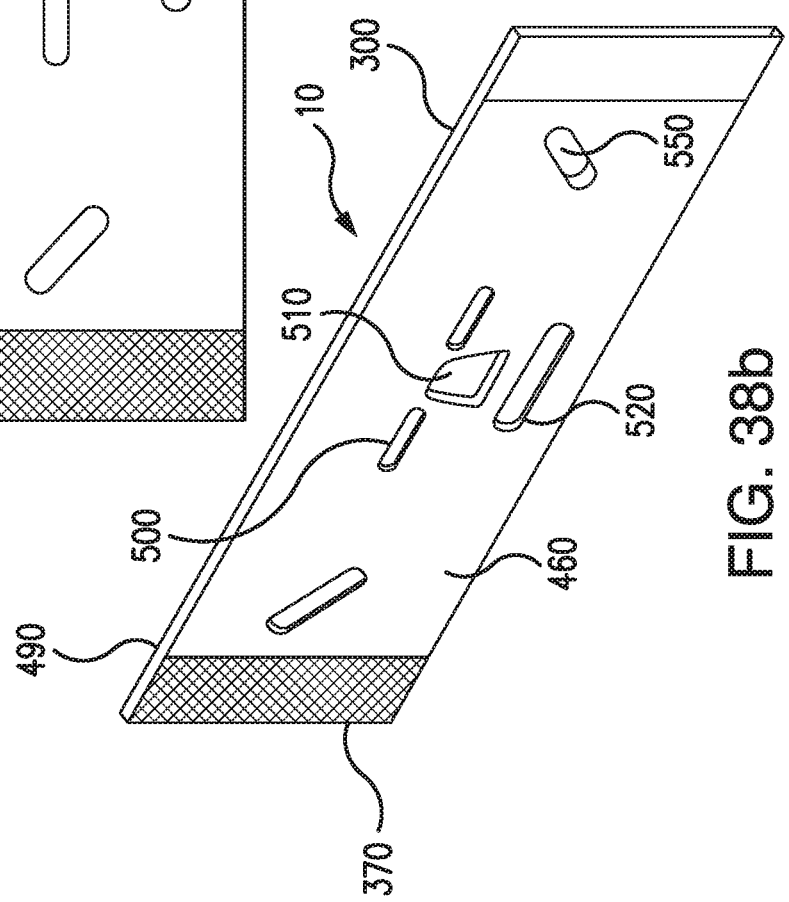

FIGS. 37(a), 37(b), 38(a), and 38(b) depict another embodiment of the treatment garment 10 in which the above discussed thermoformable assembly is included on or within an elongate strap 460 and is configured to apply compression. The elongate strap 460 preferably includes sufficient elasticity to stretch over portions of the wearer's head (e.g., completely around the wearer's head), and the strap further preferably includes hook and loop fasteners 370, 380 positioned at opposite ends of the strap that preferably span the entire width the elongate strap 460. The elasticity of elongate strap 460 coupled with the hook and loop fastener widths allow for the compression mask to be properly secured to the wearer's head while concurrently ensuring maximum compression when compared to other conventional designs that lack elasticity and/or hook and loop fasteners having the above discussed features. Also, in this aspect, this treatment garment 10 includes an outer fabric layer 490 (i.e., portion of the elongate strap or the entire elongate strap) as disclosed above and a styrene based gel 290 as disclosed above that can be detachably positioned. In certain aspects, this treatment mask 10 includes eyeholes 500, a nosehole 510, a mouth hole 520, and optionally earholes 550. The styrene based gel 290 of this mask may be adapted to cover portions of the wearer's cheeks, chin, and forehead, and in some aspects, the styrene based gel 290 of this mask is adapted to additionally substantially cover portions of the wearer's head immediately adjacent either partially or completely around the wearer's ears. In some aspects, the styrene based gel of this mask is adapted to additionally substantially cover portions of the wearer's head immediately adjacent either partially or completely around the wearer's ears. To maximize compression therapy results using this mask, the mask may be initially heated (e.g., to a glass transition temperature) as described above and the shaped to the contours of the wearer's face. After shaping this mask to the contours of the wearer's face, the mask may be allowed to harden to achieve a rigidly shaped structure and then subsequently secured onto the wearer's face using the hook and loop fasteners. If cold compression therapy or thermal therapy is further desired, the shaped mask may be chilled or heated to a sufficient temperature and the chilled or heated mask may be subsequently secured on the wearer's face. FIG. 37(b), depicts treatment mask 10 in use in which gel layer 290 is placed on bandage 470, which directly covers flesh and/or post-surgical site 480.

Figure 32:
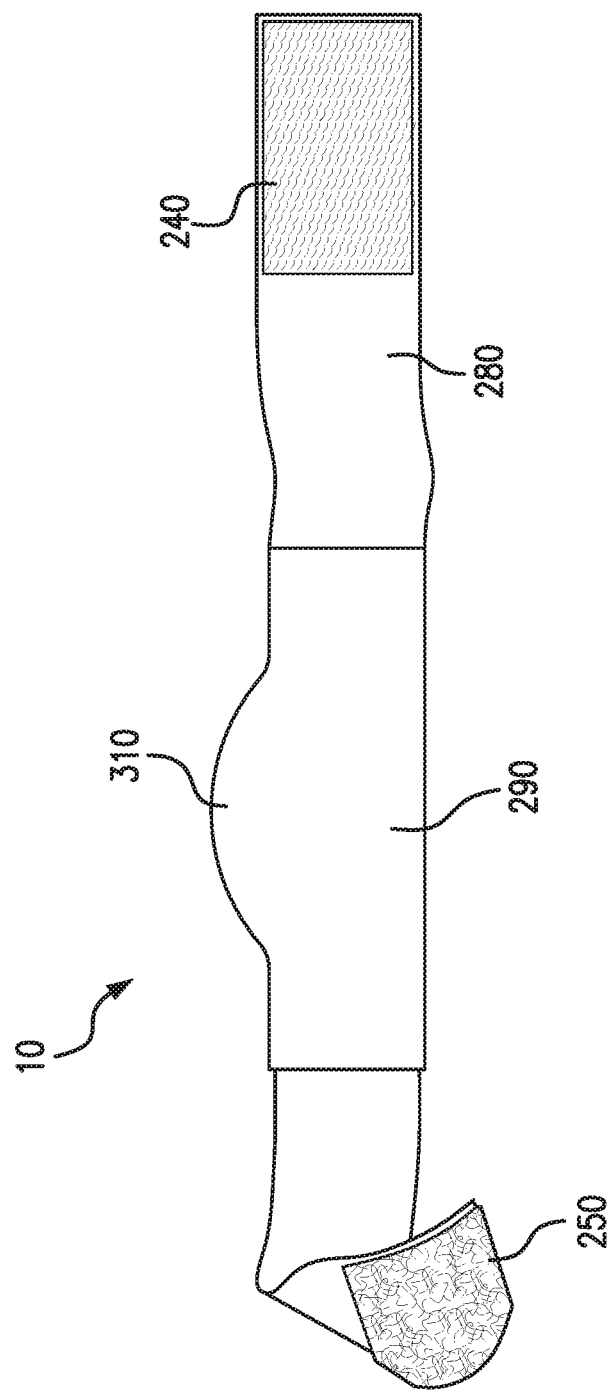
FIGS. 32 and 33 show multiple views of a garment according to another embodiment including the styrene based gel permanently positioned on an elongate, plastic bandage and adapted for application to a wearer's chin.
Figure 33:
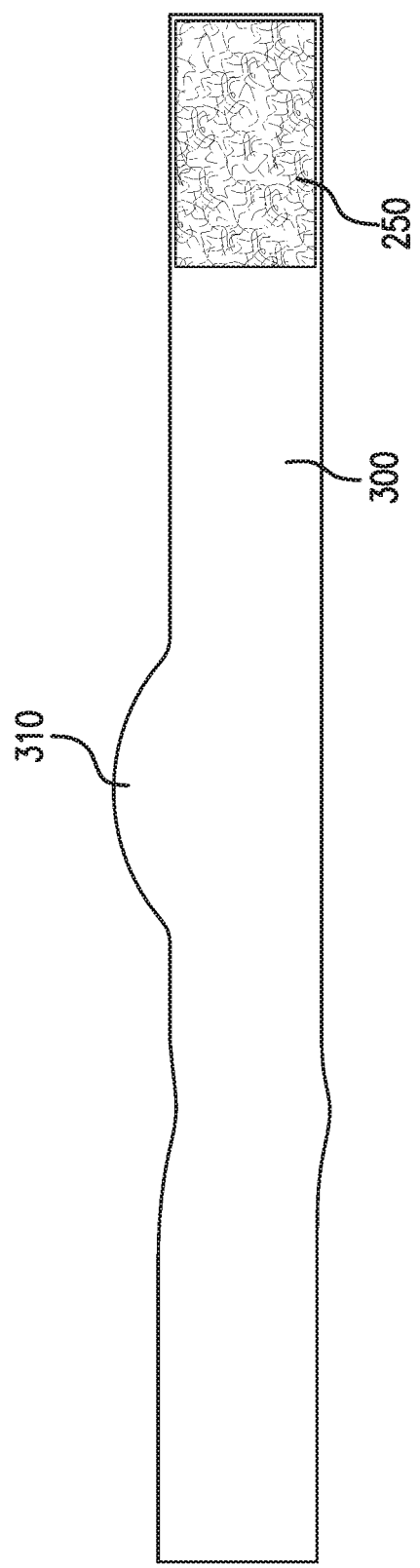

The garments disclosed herein may further include many different shapes and embodiments having a wide variety of uses. For example, these garments may be adapted for specific body parts and specific surgical procedures, which include, but are not limited, liposuction and surgical procedures involving the chin (e.g., chin implants), neck (e.g., a neck lift), etc. As shown in FIG. 31, another embodiment of the treatment garment 10 may include the styrene based gel 290 permanently positioned on an elongate, elastic bandage 280 and used to apply post-surgical compression and/or for thermal therapy and/or cold compression therapy. In this aspect, a hook fastener (not shown) may be attached one end of the elongate, elastic bandage and may fasten directly to another portion of the elongate, elastic bandage. Alternatively, the elongate, elastic bandage may include complementary hook and loop fasteners (not shown) positioned on opposite ends of the elongate, elastic bandage such that a this garment may be securely fastened to a wearer. As further illustrated in FIGS. 32 and 33, another embodiment of the treatment garment 10 may include the styrene based gel 290 being permanently positioned on an elongate, elastic bandage 280 and adapted for use on the chin, neck, or a combination thereof. In this aspect, FIGS. 32 and 33 particularly depict treatment mask 10 as useful, for example, in post-chin augmentation applications. The garment depicted in FIGS. 32 and 33 may include an arcuate shaped portion 310 of the gel and the elongate, elastic bandage adapted to cover a portion or substantially all of the wearer's chin.

Figure 39:
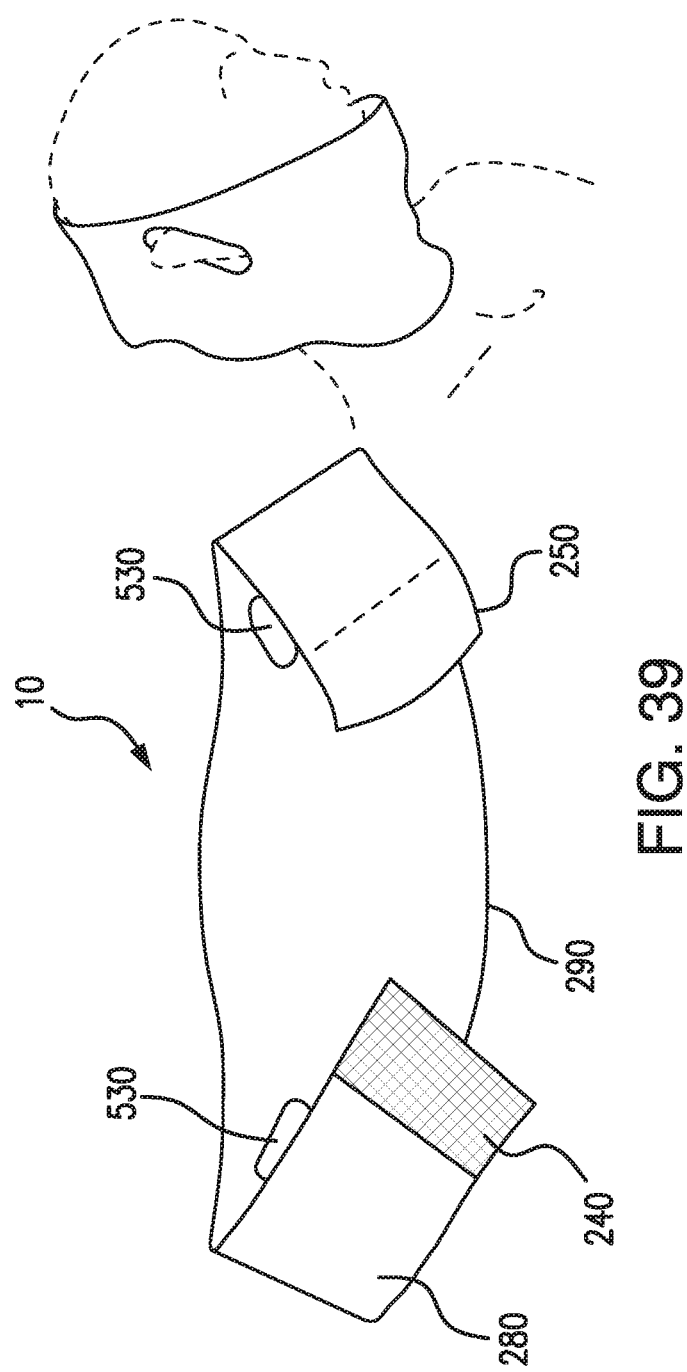
FIG. 39 shows a garment including the styrene based gel positioned on an elongate, elastic bandage and adapted for application to a wearer's chin and neck.

As shown in FIG. 39, in certain embodiments it is advantageous to provide a treatment garment 10 having a substantial strength and sufficient width to provide robust neck and chin support post-surgical procedures involving the neck (e.g., a necklift, a necklift and chin augmentation, etc.). In this aspect, treatment garment 10 is very similar to mask 180. For example, treatment garment k 10 includes the styrene based gel 290 positioned on an elongate, elastic bandage 280. Treatment garment 10 further includes complimentary hook and loop fasteners 240, 250 positioned on opposing ends of treatment mask 10. However, treatment mask 10 further includes earholes 530 from which a wearer's ears may protrude through when wearing treatment mask 10. Treatment mask 10 provides robust support to wearer's neck following post-surgical neck procedures. In addition, portions of the treatment mask 10 positioned in between earholes 530 have a greater width than (i) portions of the garment extending between each earhole 530 and each portion of the hook or loop fastener 240, 250. In other words, portions of the treatment mask 10 are tapered relative to the width of garment positioned between earholes 530. These earholes 530 and tapered features may be particularly preferred to provide robust support of a wearer's neck that further aids and expedites healing of the neck and/or chin following surgical procedures.

Figure 34:
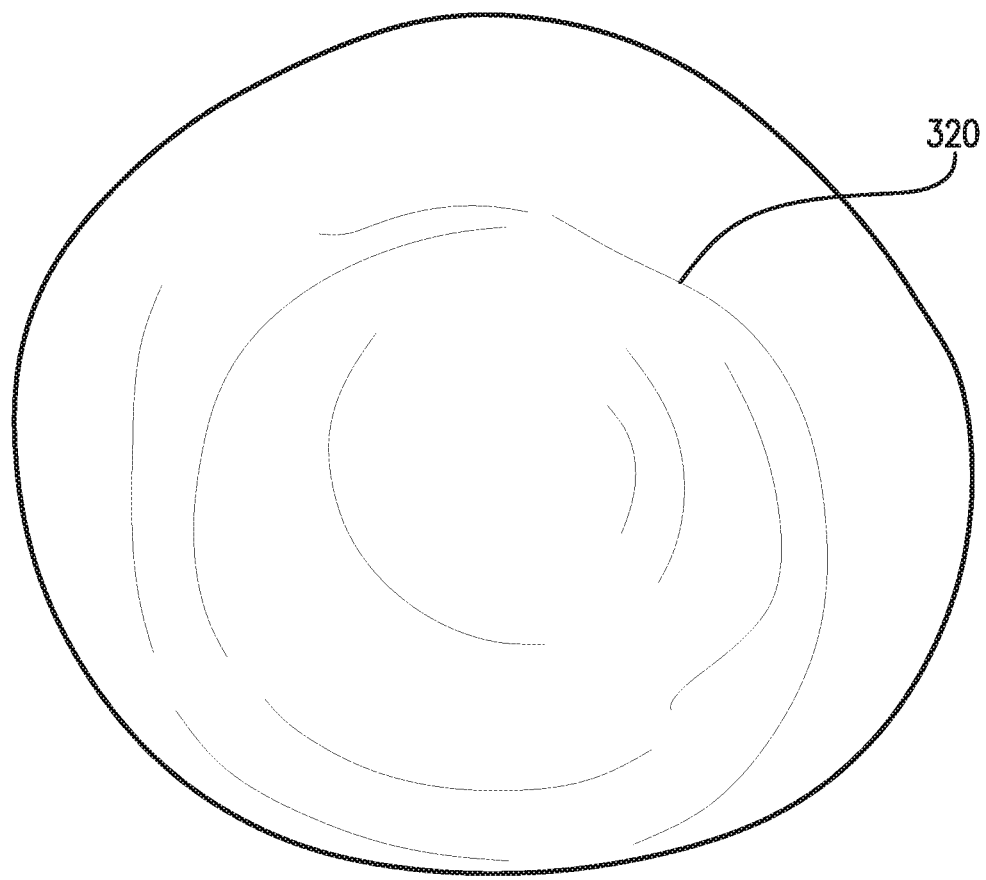
FIG. 34 is another embodiment including the styrene based gel adapted to conform to a wearer's breast.

As illustrated in FIG. 34, in another embodiment, breast cup 320 includes the styrene-based polymeric gel adapted to conform to and cover a breast following a surgical procedure, which includes, but is not limited to breast augmentation, breast reconstruction, breast reduction, or combination thereof. In this aspect, the styrene-based polymeric gel may be molded (e.g., injection molded) to have the general shape and circumference of the breast. After placing this styrene-based polymeric gel over a user's breast, this gel may be further secured to a wearer with an elongate, elastic bandage being wrapped around the wearer's breast. In this aspect, the styrene-based polymeric gel may further include a thickness of 0.1 inches to 0.5 inches, 0.15 inches to 0.3 inches which advantageously ensures maximum reduction and/or prevention of post-surgical, excessive bruising, swelling, and edema associated with surgical procedures and further aids in the beneficial effects of thermal therapy and cold compression therapy. In certain aspects, breast cup 500 is packaged or included within a kit that further includes at least one elongate, elastic strap such as any of the above disclosed elongate, elastic straps, the strap being configured to hold breast cup 500 on a wearer's breast while applying adequate pressure to potentially reduce bruising, swelling, and/or edema at the surgical site.

Figure 40:
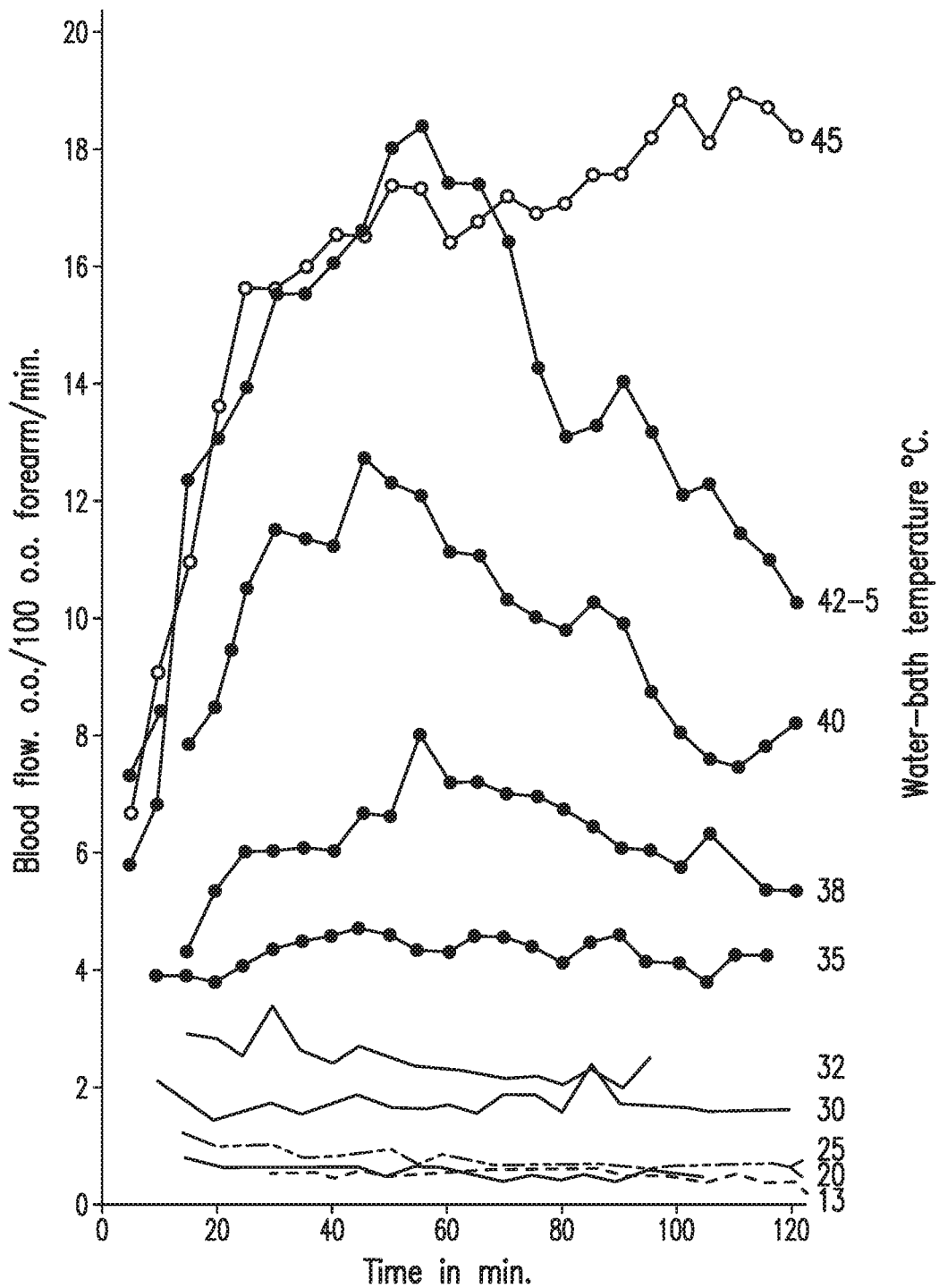
FIG. 40 shows a graph depicting the relationship between temperature and blood flow.

The benefits of the present invention can be seen in FIG. 40. As can be seen in the graph, as temperature increases, blood flow levels increase. Thus, the use of the thermoplastic elastomer in combination with the treatment garment 10

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A treatment garment for treatment of a surface comprising:
    a thermoformable composite further comprising a single, continuous thermoplastic elastomer gel layer having a thickness between 0.1 to 0.625 inches and comprising a styrenic triblock copolymer where the triblock copolymer is a selected amount of one or more of hydrogenated poly(styrene-b-isoprene), hydrogenated poly(styrene-b-isoprene-b-styrene), hydrogenated poly(styrene-b-butadiene-b-styrene), hydrogenated poly(styrene-b-isoprene/butadiene-b-styrene), or polyethylene, 50 to 90 percent by weight of a plasticizing agent, a latent heat of fusion agent comprising at least one paraffin, and an additive, the thermoplastic elastomer gel layer arranged on the thermoformable composite arranged between an outer layer and further comprising a fabric layer bonded to the outer layer and the fabric layer having a mass ranging from 110 to 160 denier, the thermoformable composite configured to be heated to a glass transition temperature of the thermoplastic elastomer gel layer such that the thermoformable composite can be shaped to conform to contours of the surface.

2. The treatment garment of claim 1 further comprising at least one strap configured to secure around a user's head to hold the treatment garment in place having a first end and a second end with a hook and loop fastener at the first end for securing the strap to the treatment garment.

3. The treatment garment of claim 2, wherein the strap is bifurcated at the first end and the second end.

4. The treatment garment of claim 1, wherein the thermoplastic elastomer experiences a solid-solid phase transition whenever the thermal capacity agent melts into liquid form.

5. The treatment garment of claim 4, wherein the outer layer has multidirectional stretch.

6. The treatment garment of claim 1 further comprising a series of holes through the outer layer and through the thermoplastic elastomer gel layer shaped to receive orifices.

7. The treatment garment of claim 1, wherein the thermoformable composite is configured to be heated to a temperature of no more than 80° F. above the glass transition temperature of the thermoplastic elastomer gel layer.

8. The treatment garment of claim 1, wherein the outer layer is continuous.

9. The treatment garment of claim 1, wherein the thermoplastic elastomer gel layer is removable from the thermoformable composite.

10. The treatment garment of claim 1, wherein the thermoplastic elastomer gel layer has a thermal-conductivity of 0.05 to 3.00 W/mk.

11. The treatment garment of claim 1, further comprising two straps configured to secure around a user's head to hold the treatment garment in place on the user's face.

12. The treatment garment of claim 1, wherein the treatment garment is a partial face mask.

13. The treatment garment of claim 1, wherein the plasticizing agent is a plasticizing oil.

14. The treatment garment of claim 1, wherein the additive is an antioxidant.

15. The treatment garment of claim 1, wherein the additive is an antimicrobial agent.

16. The treatment garment of claim 1, wherein the thermoplastic elastomer gel layer contains 0.5 to 30 percent by weight of additive and 3 to 50 percent by weight of the latent heat of fusion agent.

17. A treatment garment comprising:
a thermoformable assembly comprising a thermoformable body arranged on an outer layer, the thermoformable assembly configured to be heated to a glass transition temperature of the thermoformable body such that the thermoformable assembly can be shaped to conform to contours of a user's face upon heating and cooling;
a fabric layer bonded to the outer layer wherein the fabric layer has a mass ranging from 110 to 160 denier; and
a single, continuous thermoplastic elastomer gel layer having a thickness between 0.1 and 0.625 inches arranged within the thermoformable assembly.

18. The treatment garment of claim 17, wherein the thermoplastic elastomer gel layer further comprises a triblock copolymer, a plasticizing agent, a paraffinic substance, and an additive.

19. The treatment garment of claim 18, wherein the triblock copolymer is a selected amount of one or more of hydrogenated poly(styrene-b-isoprene), hydrogenated poly(styrene-b-isoprene-b-styrene), hydrogenated poly(styrene-b-butadiene-b-styrene), hydrogenated poly(styrene-b-isoprene/butadiene-b-styrene), or polyethylene.

20. The treatment garment of claim 18, wherein the plasticizing agent is a plasticizing oil.

21. The treatment garment of claim 18, wherein the additive is an antioxidant.

22. The treatment garment of claim 18, wherein the additive is an antimicrobial agent.

23. The treatment garment of claim 18, wherein the thermoplastic elastomer gel layer contains 50 to 90 percent by weight of plasticizing oil, 0.5 to 30 percent by weight of additive, and 3 to 50 percent by weight of a latent heat of fusion agent.

24. The treatment garment of claim 17, wherein the thermoplastic elastomer gel layer is removable.

25. A treatment garment comprising:
a garment further comprising a single, continuous thermoplastic elastomer gel layer inside an outer layer shaped to conform to and cover a wearer's face including a chin, a nose, cheeks, forehead, and ears, the mask having a series of openings after being heated and cooled, the thermoplastic gel layer having a thickness between 0.1 and 0.625 inches and further comprising a thermoplastic elastomer gel layer, 50 to 90 percent by weight of a plasticizer, and a latent heat of fusion agent comprising at least one paraffin;
a fabric layer bonded to the outer layer wherein the fabric layer has a mass ranging from 110 to 160 denier; and
a strap configured to fasten around the forehead and under the chin to secure the garment in place.

26. A method for the application of additives to a surface of skin comprising:
applying an additive to a treatment garment, the treatment garment further comprising a thermoformable composite further comprising a single, continuous thermoplastic elastomer gel layer having a thickness between 0.1 and 0.625 inches and comprising a styrenic triblock copolymer where the triblock copolymer is a selected amount of one or more of hydrogenated poly(styrene-b-isoprene), hydrogenated poly(styrene-b-isoprene-b-styrene), hydrogenated poly(styrene-b-butadiene-b-styrene), hydrogenated poly(styrene-b-isoprene/butadiene-b-styrene), or polyethylene, 50 to 90 percent by weight of a plasticizing agent, a thermal capacity agent comprising at least one paraffin, and an additive, arranged on the thermoformable composite arranged between an outer layer and a fabric layer bonded to the outer layer wherein the fabric layer has a mass ranging from 110 to 160 denier, the thermoformable composite configured to be heated to a glass transition temperature of the thermoplastic elastomer gel layer such that the thermoformable composite can be shaped to conform to contours of a user's face;
heating the treatment garment such that the thermoplastic elastomer gel layer reaches a glass transition temperature;
applying the treatment garment to the surface;
removing the treatment garment from the surface when the thermoplastic elastomer gel layer goes below the glass transition temperature.

* * * * *